(12) United States Patent
Hyde, Jr.

(10) Patent No.: US 6,589,281 B2
(45) Date of Patent: Jul. 8, 2003

(54) TRANSOSSEOUS CORE APPROACH AND INSTRUMENTATION FOR JOINT REPLACEMENT AND REPAIR

(76) Inventor: Edward R. Hyde, Jr., 450 El Camino Real #524, Menlo Park, CA (US) 94025

( * ) Notice: Subject to any disclaimer, the term of this patent is extended or adjusted under 35 U.S.C. 154(b) by 39 days.

(21) Appl. No.: 09/761,227

(22) Filed: Jan. 16, 2001

(65) Prior Publication Data

US 2002/0095214 A1 Jul. 18, 2002

(51) Int. Cl.[7] .................................................. A61F 2/30
(52) U.S. Cl. ................................................ 623/18.11
(58) Field of Search ........................ 623/18.11, 19.11, 623/20.11, 20.14, 22.11, 21.11, 23.39, 902; 606/53; 128/898

(56) References Cited

U.S. PATENT DOCUMENTS

| | | |
|---|---|---|
| 3,675,656 A | 7/1972 | Hakim |
| 3,846,846 A | 11/1974 | Fischer |
| 4,550,450 A | 11/1985 | Kinnett |
| 4,946,462 A * | 8/1990 | Watanabe ................... 606/148 |
| 4,978,323 A | 12/1990 | Freedman |
| 5,057,108 A * | 10/1991 | Shetty et al. ................. 606/53 |
| 5,059,203 A | 10/1991 | Husted |
| 5,176,618 A | 1/1993 | Freedman |
| 5,234,433 A | 8/1993 | Bert et al. |
| 5,358,524 A | 10/1994 | Richelsoph |
| 5,458,646 A | 10/1995 | Giachino et al. |
| 5,496,326 A * | 3/1996 | Johnson ....................... 606/88 |
| 5,507,833 A | 4/1996 | Bohn |
| 5,570,706 A * | 11/1996 | Howell ....................... 128/898 |
| 5,595,563 A | 1/1997 | Moisdon |
| 5,693,054 A | 12/1997 | Durham et al. |
| 5,702,486 A | 12/1997 | Craig et al. |
| 5,769,856 A | 6/1998 | Dong et al. |
| 5,776,136 A | 7/1998 | Sahay et al. |
| 5,779,710 A | 7/1998 | Matsen et al. |
| 5,800,551 A | 9/1998 | Williamson et al. |
| 5,807,401 A | 9/1998 | Grieshaber et al. |
| 5,885,297 A | 3/1999 | Matsen, III |

(List continued on next page.)

FOREIGN PATENT DOCUMENTS

DE    196 54 990 A 1    10/1996

OTHER PUBLICATIONS

Levy et al., "Howmedica Surgical Techniques: The Howmedica Precision Hip System," Howmedica, Inc., Rutherford, NJ, Pfizer Hospital Products Group (1988 & 1991).

Primary Examiner—Eduardo C. Robert
(74) Attorney, Agent, or Firm—Pennie & Edmonds LLP

(57) ABSTRACT

The present invention relates to a method and instrumentation for gaining access to areas in and around joints for treatment and to provide new implants and instrumentation adapted for the new method. In a transosseous core approach of the present invention, the joint is entered through a pathway provided in a portion of a joint bone. Such pathway is preferably made by taking out a bone core from the bone in or adjacent to the joint, wherever possible without substantially compromising physical integrity and physiological viability of the joint. Typically the main route for the transosseous core approach traverses through a more-accessible bone of the joint which can be aligned with a less-accessible bone of the joint in order to facilitate treatment of articular surfaces and/or other structures in the joint. The transosseous pathway into the joint is preferably provided by novel surgical instruments such as a core cutter, cartilage punch, hemostatic device, and retractable axial/transaxial cutting device. Implants modules are also provided which can be inserted into the joint through the transosseous pathway and assembled in situ inside the joint to form an implant assembly.

42 Claims, 21 Drawing Sheets

U.S. PATENT DOCUMENTS

| | | | |
|---|---|---|---|
| 5,895,404 A | | 4/1999 | Ruiz |
| 5,931,869 A | * | 8/1999 | Boucher et al. .............. 623/13 |
| 5,961,555 A | | 10/1999 | Huebner |
| 6,051,751 A | | 4/2000 | Sioshansi et al. |
| 6,102,956 A | | 8/2000 | Kranz |
| 6,110,211 A | * | 8/2000 | Weiss ..................... 623/23.11 |
| 6,228,119 B1 | | 5/2001 | Ondria et al. |
| 6,284,002 B1 | | 9/2001 | Sotereanos |
| 6,290,725 B1 | | 9/2001 | Weiss et al. |
| 6,375,684 B1 | * | 4/2002 | Kriek ..................... 623/23.39 |
| 2002/0013623 A1 | * | 1/2002 | Sklar ..................... 623/13.17 |

* cited by examiner

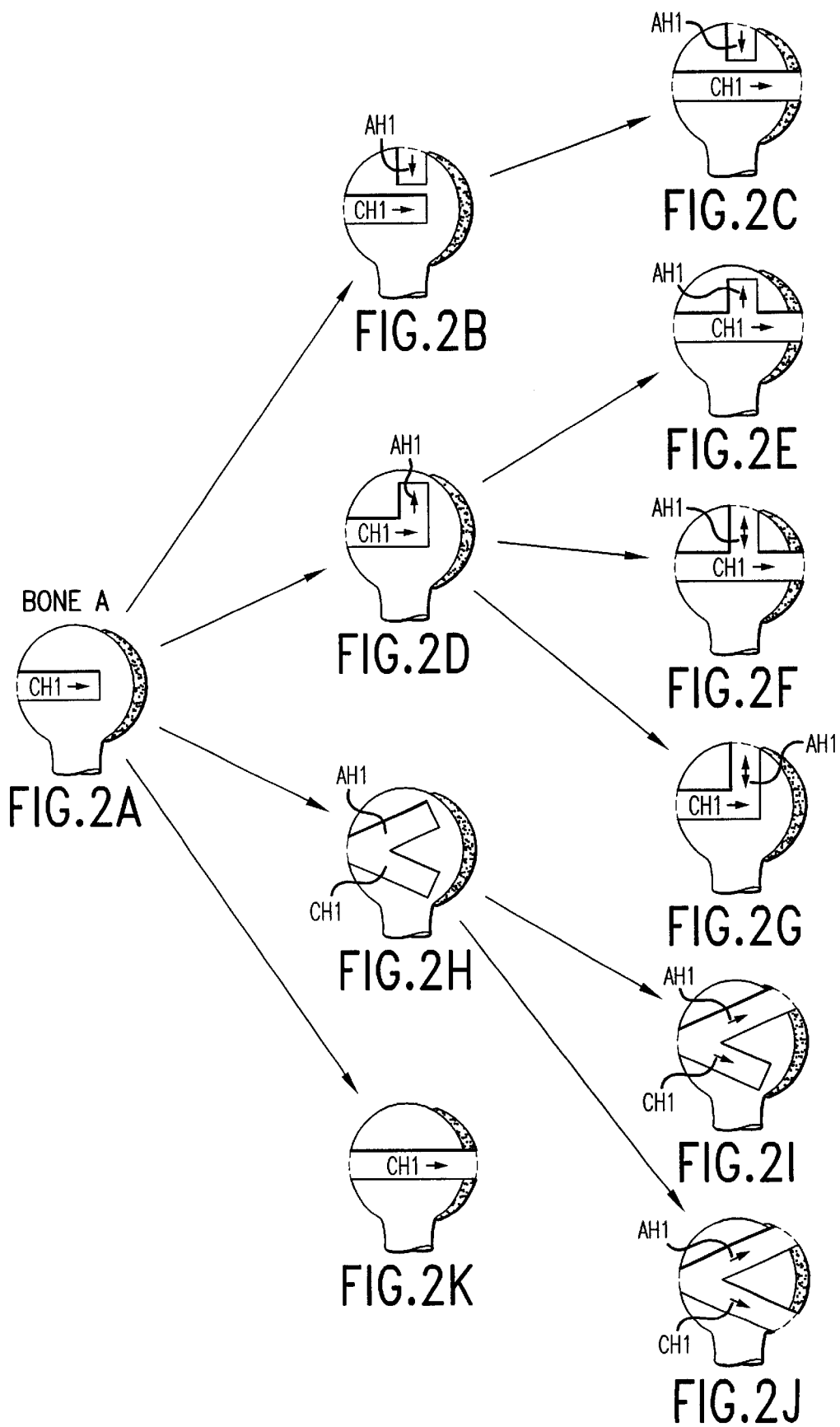

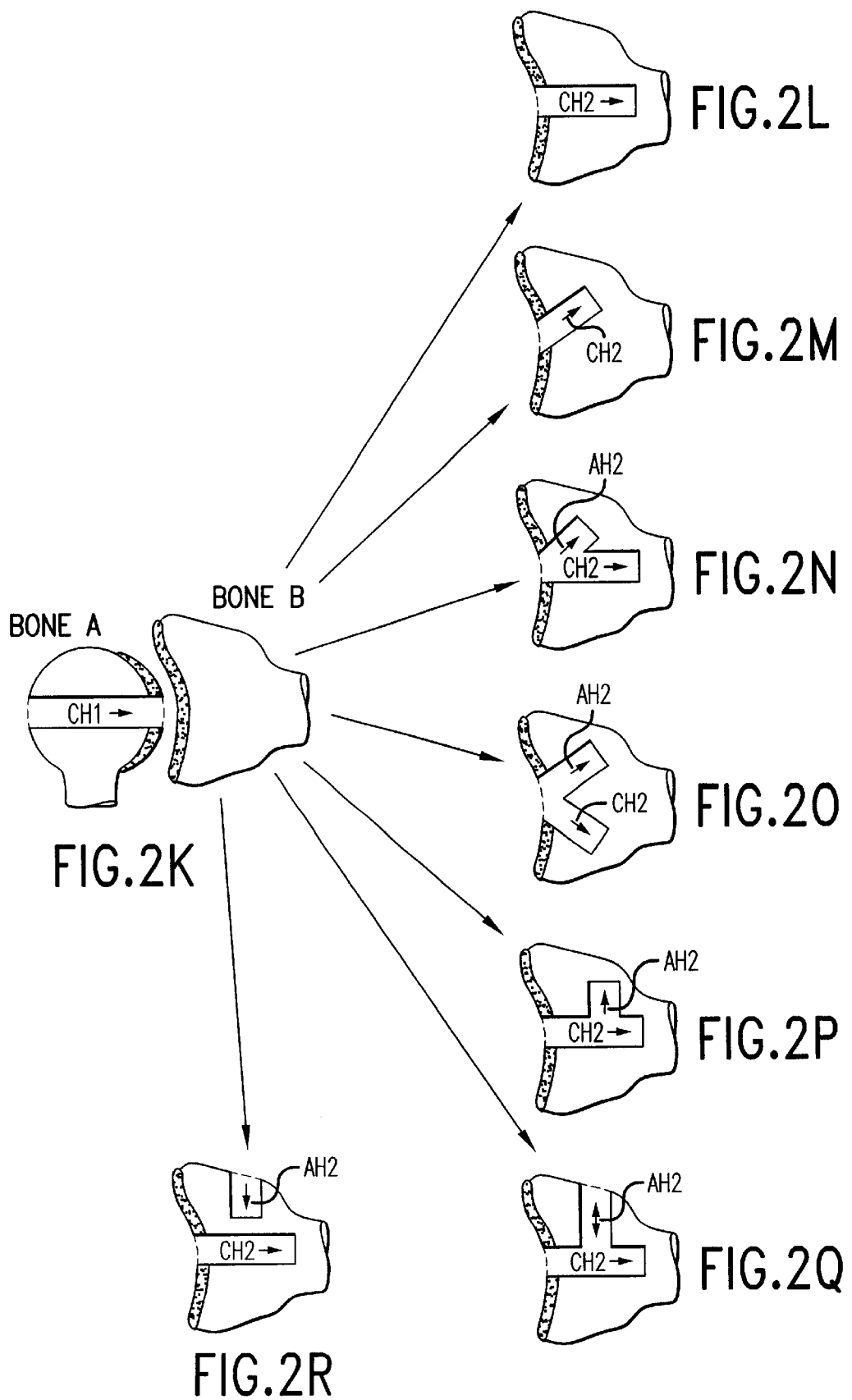

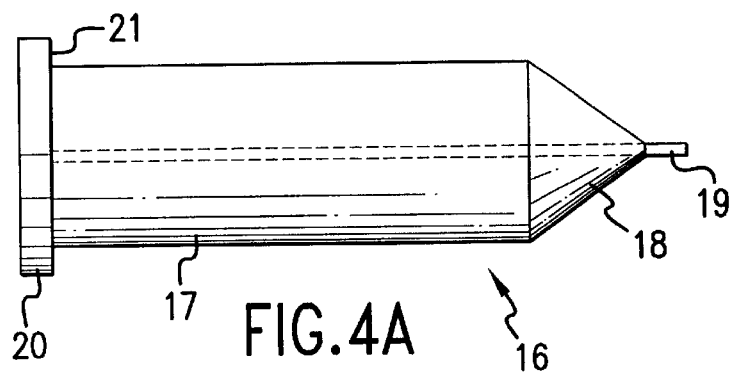
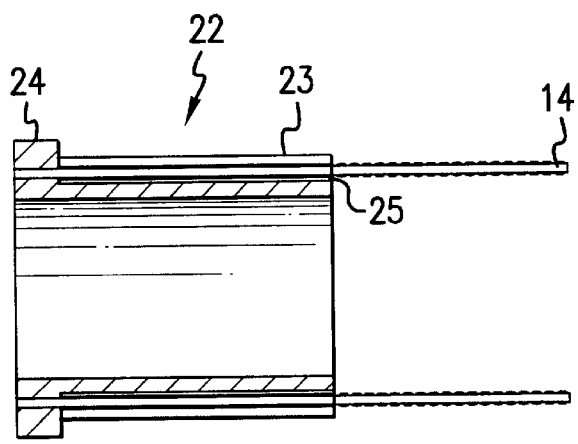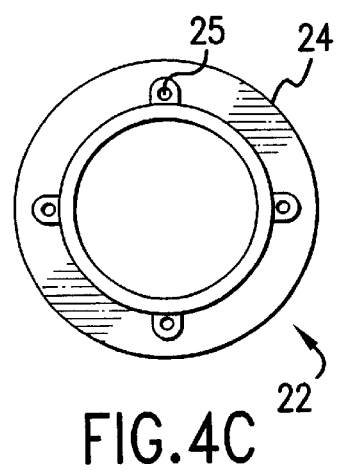

TRANSOSSEOUS CORE APPROACH AND INSTRUMENTATION FOR JOINT REPLACEMENT AND REPAIR

FIELD OF THE INVENTION

The present invention relates to instrumentation, implants, and techniques for orthopedic surgery and, more particularly, to a transosseous core approach for joint repair, replacement, and/or treatment, wherein the treatment site is approached through a transosseous pathway constructed by taking a bone core out of a bone, at the joint.

BACKGROUND OF THE INVENTION

An orthopedic surgeon may wish to gain entry to a particular joint for multiple reasons. The surgeon may wish to alter or remove a defect in the joint, to replace an articular surface of the joint or the entire joint (i.e., total joint arthroplasty), to transplant cartilage autographs/implants and/or to alter the characteristics of soft tissues in and around the joint such as tendons, ligaments, joint capsule, etc. In a typical joint, the articular surfaces of the joint are surrounded by soft tissue structures, injury to which is often undesirable or at least to be minimized. FIG. 1 schematically illustrates a typical joint (representative of diarthroses) and surrounding anatomical structures of the joint. The exemplary joint includes first bone "A" and second bone "B", each including the articular surface 1A, 1B comprising articular cartilage enclosed within a synovial lining 2. Articular surfaces 1A, 1B and synovial lining 2 are in turn surrounded by a joint capsule 3 on which a bursa 5 may be disposed. The synovial lining is also referred to as the synovial stratum, which together with the fibrous stratum, make up the articular capsule. Bones A, and B are attached to tendon 6 and muscle 7 and are coupled to each other by ligaments 4. Blood vessels and nerves (not shown) generally run with muscle 7, tendon 6, and/or ligaments 4. Each bone A, B includes portions of non-articular surface 8A, 8B outside joint capsule 3 that are substantially clear of the above-mentioned soft tissue structures of the joint.

Conventional methods for gaining access into the joints typically require wide exposures and joint dislocation. See for example U.S. Pat. No. 4,550,450, entitled "Total Shoulder Prosthesis System," and U.S. Pat. No. 5,507,833, entitled "Hip Replacement and Method for Implanting The Same." These classical wide exposures damage large area of tissue, create large scars, jeopardize neurovascular structures, produce considerable blood loss, increase the potential for other significant complications, and increase the risk of infection. Wide exposures, because of their inherent nature, traumatize tissues as they are cut, retracted, and/or divided. The amount of tissue disrupted increases the healing time and the physiological strain on the patient because the amount and severity of postoperative pain correlate directly to the size of the incision and extent of surgery. Traditional wide exposures can also create limits on the functional results of surgery to treat joint problems by the sequlae introduced by the exposure itself. More recent developments in arthroscopic techniques may reduce the amount of trauma to which a patient may be subjected, but many procedures are not amenable to arthroscopic techniques and frequently such procedures still entail damage to soft tissue structures surrounding the joint such as the articular capsule.

Patient cooperation is an important factor in postoperative rehabilitation. The ultimate result of the treatment of joint problems hinges to a major degree on this fact. Postoperative pain which is proportional to the incision size, exposure, and/or tissue damage, inhibits the rate of patient's rehabilitation. The inability to reach desired rehabilitation goals often results in an overall inferior and/or an unsatisfactory result. These additional drawbacks of conventional joint surgical exposures and treatments contribute to reduce the ultimate outcome of the surgical intervention, often introducing unwanted and unnecessary sequlae.

SUMMARY OF THE INVENTION

In the present invention, a joint is entered via a route passing through a pathway provided in a portion of a joint bone. Such pathway is made by taking out a bone core from the bone in or adjacent to the joint without substantially compromising physical integrity and physiological viability of the joint. Typically the main route for the present invention traverses through a more-accessible bone of the joint which can be aligned with a less-accessible bone of the joint to facilitate treatment of the articular surfaces and/or other structures in the joint.

The present invention thus provides a new method and instrumentation for gaining access to areas in and around the joint surfaces to treat problems of the joint as well as to provide new implants and instrumentation adapted for the new method. The transosseous core approach of the present invention has at least two main advantages over conventional surgical exposures. A first is that the present invention requires substantially smaller incisions than standard exposures. A second is that the present invention does not substantially interfere with normal anatomical structures surrounding the joint such as vascular, nervous, muscular, ligamentous, and other soft tissues of the joint and, therefore, is less invasive. Additionally, in many cases the exposure obtained by the transosseous core approach provides better and more direct access to areas of the joint not found in current exposures.

Every joint includes at least two bones arranged to allow movement thereof. Each bone includes an articular surface substantially enclosed within a joint capsule and a non-articular surface (e.g., a superficial portion thereof) disposed substantially outside the joint capsule. The present invention is based on the transosseous core approach where the articular surface of the bone and other tissues within the joint capsule can be accessed through a pathway (such as the hole) in the bone commencing from its non-articular surface and approaching its articular surface.

Accordingly, in one aspect of the present invention, a method may be provided to treat the joint by positioning the first bone with respect to the second bone, by removing a bone core from the first bone along a first axis to provide a bone core hole beginning in a first region of the first bone and approaching the first articular surface of the first bone without penetrating its articular surface wherein the first region is its non-articular surface, by performing an intervention through the bone core hole, and by replacing at least portion of the first bone core within the bone core hole. Such intervention may be implanting at least one component of a prosthetic device within the first bone core hole.

Alternatively, the method may be provided for treating the joint by positioning the first bone with respect to the second bone, by cutting the first bone starting from its first region (e.g., the first non-articular surface thereof) and approaching its first articular surface, and by ceasing cutting at a point adjacent the first articular surface without penetrating it, thereby providing the first bone with an elongated first core hole capable of receiving an implant. The first region is generally the first non-articular surface of the first bone and, preferably, superficial to a surface of a body part such as limbs.

In another aspect of the invention, an access is provided to the joint including at least one more-accessible bone, at least one less-accessible bone, and the surrounding anatomical structures by positioning the more-accessible bone with respect to the less-accessible bone, by cutting the more-accessible bone starting from a first region and approaching its articular surface, wherein the first region is its non-articular surface, and by ceasing cutting at a point adjacent the articular surface of the more-accessible bone without penetrating it. Accordingly, the more-accessible bone is provided with a more-accessible core hole providing the access to a portion of the more-accessible bone which is substantially proximate to its articular surface.

In the alternative, a method may also be provided for an access to the joint by positioning the first bone with respect to the second bone, cutting out a core portion of the first bone starting from the first non-articular surface of the first bone and approaching the first articular surface of the first bone, where the core portion of the first bone is not coupled to the surrounding anatomical structures of the joint, and by ceasing cutting at a point adjacent the first articular surface of the first bone without penetrating it. Therefore, without detaching the surrounding anatomical structures from the first bone, the first bone can be provided with a first core hole configured to receive an implant.

In yet another aspect of the invention, a method for providing an access to the joint by positioning the first bone with respect to the second bone, by incising at most a portion of the joint capsule, by cutting out a core portion of the first bone starting from an exterior portion of the first bone and approaching an interior portion of the first bone, and ceasing cutting at a point of the first bone disposed inside the joint capsule. Thus, without substantially compromising integrity of the joint capsule, the first core hole can be provided to the first bone. A skin, fascia, fat layer, and/or soft tissues disposed on or adjacent the exposed portion of the first bone may be incised and a muscle may be divided in a direction of its main fibers. Blood vessels and nerves may also be disposed away from the exposed portion of the first bone.

In another aspect of the invention, a method is provided for treating a joint by positioning the first bone with respect to the second bone, by cutting a hole in the first bone along a first axis beginning in the first bone first region and passing through the first bone articular surface, by continuing cutting the hole through the second bone articular surface and into the second bone, by terminating cutting of the hole within the second bone, and by implanting at least one component of a prosthetic device within the second bone hole by passing the component through the first bone hole.

In a further aspect, another method is provided for treating a joint by positioning the first bone with respect to the second bone, by cutting a hole having a first diameter in the first bone along a first axis beginning in the first bone first region and passing through the first bone articular surface, by continuing cutting the hole through the second bone articular surface and into the second bone, by enlarging the hole to a second diameter greater than the first diameter at a location spaced away from the first bone first region, and by implanting at least one component of a prosthetic device within the enlarged hole by passing the component through the hole with the first diameter.

The present invention further provides various orthopedic implants (including implant assemblies and modules thereof) for the transosseous core method and devices therefor.

In one aspect of the invention, an orthopedic implant assembly is provided which is arranged to be implanted adjacent to or in the joint through a pathway formed inside the joint bone and having an effective pathway dimension. Such implant assembly includes at least two implant modules each of which is configured to have an effective module dimension no greater than the effective pathway dimension so as to allow passage of the implant module through the pathway. Each implant module is configured to couple with at least one of the others to form the implant assembly in situ having an effective assembly dimension which is no less than both of the effective pathway dimension and effective module dimension.

In another aspect, a surgical kit is provided to include a bone cutting tool having a cutting element for creating a bone hole of a first diameter, and a bone prosthesis assembly with at least two implant modules configured and dimensioned to be separately inserted through the bone hole of the first diameter and to mate together at a site of interest to form said assembly. The surgical kit also includes a surgical hemostat for treating the wall of the bone hole. The hemostat comprises an applicator expandable from a retracted position to a expanded position, a cylindrical, expandable sleeve configured and dimensioned to be disposed over the applicator in the retracted position, and a hemostatic agent disposed on the sleeve, where expansion of the applicator to the expanded position within a bone hole forces the hemostatic agent against the wall. The surgical kit further includes a cartilage punch having an operative portion configured and dimensioned to be inserted through the first diameter bone hole and manipulated from outside the hole, where the operative portion typically includes a blade which surrounds a central cavity to capture cartilage cut by said blade. The surgical kit may further includes a second bone cutting tool with an operative portion configured and dimensioned to be inserted through the first diameter bone hole and manipulated from outside the hole, where the operative portion includes at least one cutting member for removing bone material to provide a larger void within the first diameter bone hole.

In another aspect, a prosthetic assembly is provided to be inserted through a bone hole having a first hole diameter and implanted at a site of interest within a bone or joint. The assembly includes at least two implant modules configured and dimensioned to be individually inserted through the bone hole and the implant modules fit together at the site of interest to form said prosthetic assembly. When assembled, the assembly has at least one dimension larger that the first hole diameter.

A surgical tool is also provided for cutting bone and includes an elongated body and a cutting member. The elongated body has a longitudinal axis and defining an opening in a distal portion thereof and the cutting member is movably disposed within the body so that the cutting member moves between a first position disposed within the body and a second position extending out of the opening for cutting bone.

In another aspect, a surgical hemostat is provided for treating walls of bone holes. Such hemostat typically includes an applicator expandable from a retracted position to a expanded position, a cylindrical, expandable sleeve configured and dimensioned to be disposed over the applicator in the retracted position, and a hemostatic agent disposed on an outer surface of the sleeve. When the applicator is expanded to the expanded position within a bone hole, the hemostatic agent is forced against the bone hole wall.

In a further aspect, an expandable surgical bone reamer includes a central member, a plurality of arms extending radially from the central member where the arms are extensible in the radial direction between retracted and expanded positions, a bone reaming member disposed on each arm opposite the central member, and an expansion mechanism operatively connected to the arms such that the distance of the bone reaming members from said central member may be controlled.

Other features and advantages of the present invention will be apparent from the following detailed description, and from the claims.

BRIEF DESCRIPTION OF THE DRAWINGS

FIGS. 2A to 2R are schematic diagrams of the joint bones treated by exemplary transosseous core approaches according to the present invention;

FIGS. 4A to 4C are views of an exemplary guide assembly according to the present invention;

DETAILED DESCRIPTION OF THE PREFERRED EMBODIMENTS

The present invention can be used to treat problems that occur in almost any joint, in particular diarthroidal joints. A common element or feature of the present invention, regardless of which joint is treated, is that the joint surface(s) to be treated are approached through a first bone, i.e., the transversed bone. This is accomplished by creating an exposure through a channel or hole that is made in the transversed bone overlying the joint surface to be addressed. Preferably, the channel is made by a transosseous core, which core can be replaced after treatment or placement of an implant to reconstitute the integrity of the bone substance or surface. In this manner, the joint surface to be treated is approached from the "back side" such that highly invasive dislocation of the joint and wide exposure incisions are not required to create the necessary access. Depending upon the degree of treatment necessary, the present invention also avoids or minimizes in appropriate cases disruption of the capsule and other soft tissue structures associated with the joint. As a further aspect of the present invention, special implants and associated instrumentation are devised to take full advantage of this less invasive approach.

The transosseous core approach according to the invention can be applied to many joints of the body for a variety of purposes. FIGS. 2A to 2R are schematic diagrams of the transosseous core approach according to the present invention, in which details of the anatomical structures of the joint are omitted for simplicity so as to provide an overview of different applications of the transosseous core approach. FIGS. 2A through 2K show only first bone "A", typically a more readily accessible bone, while FIGS. 2L through 2R only show second bone "B", typically a less accessible bone.

Figure 1:
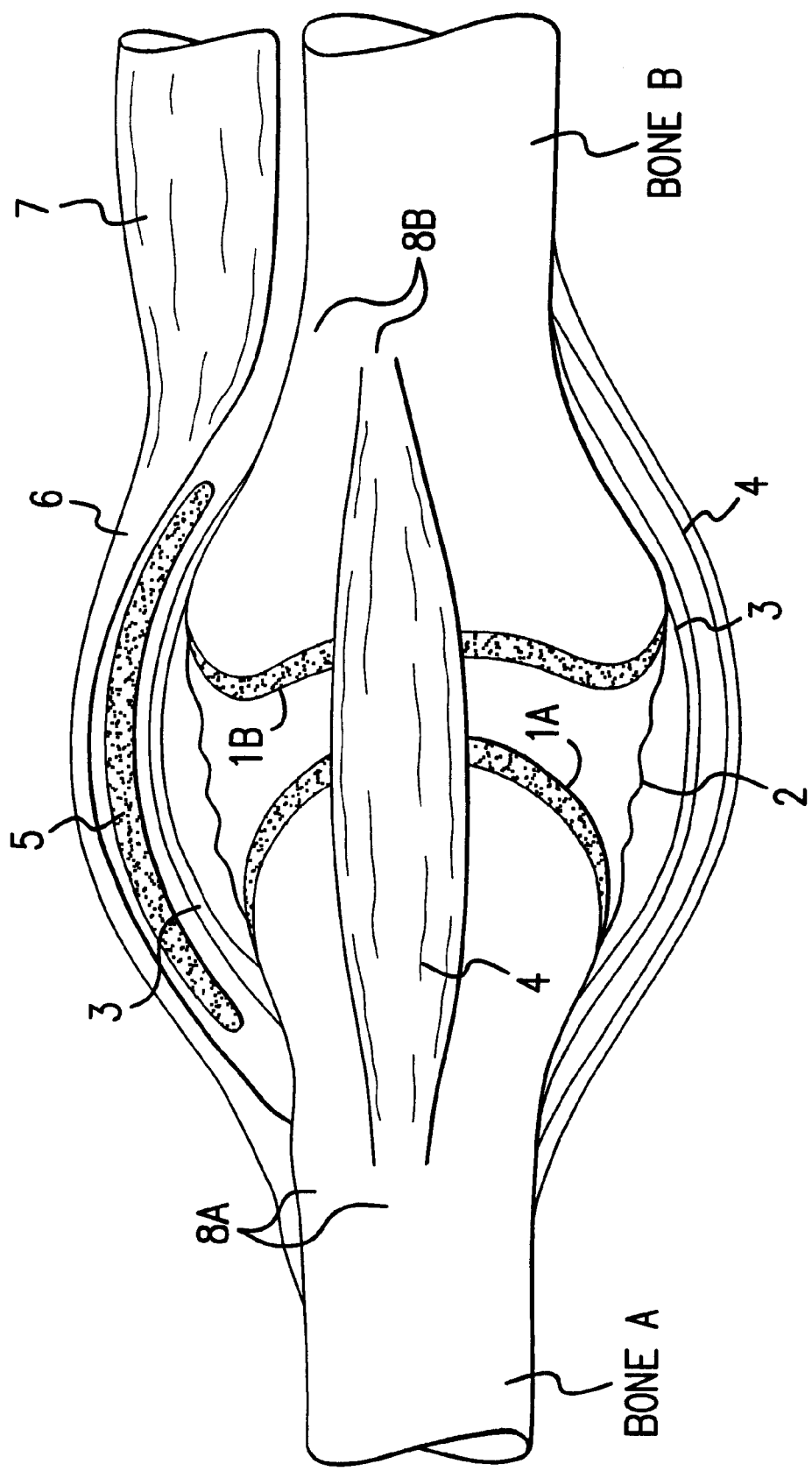
FIG. 1 is a schematic view of joint bones and surrounding anatomical structures of an exemplary joint.

As shown in FIG. 2A, first bone A is preferably cored starting from a first region (i.e., the non-articular surface of the first bone or "first non-articular surface", 8A in FIG. 1) and approaching the articular surface thereof ("first articular surface", 1A in FIG. 1). Typically the first bone hole will have a diameter approximately 10% to 30% of the bone diameter at the site of the hole. If desired, the cutting process may be stopped at any point near or adjacent the first articular surface before cutting or penetrating such.

Accordingly, the first bone is provided with a generally elongated first pathway or first core hole (designated as "CH1" in the figures) into which one or more implants may be inserted and secured. The first non-articular surface 8A is preferably superficial to a surface of a body part such as extremities and, therefore is more accessible to a surgeon for commencing drilling the first bone.

Once the first core hole is cut, one or more auxiliary holes ("first auxiliary hole" referred to as "AH1" in the figures) may be provided in a second region of the first bone. As in FIG. 2B, the second region may be an uncut portion of the first non-articular surface from which the first auxiliary hole may be drilled toward an interior of the first core hole (e.g., FIG. 2F) or toward other uncut portions of the first bone including both the non-articular and articular surfaces thereof. If desirable, the second region may also be an uncut portion of the first articular surface. As shown in FIG. 2D, the second region may be an interior of the first core hole from which the first auxiliary hole may be extended toward the uncut portion of the first bone which may be either non-articular or articular surface thereof. In the alternative, as shown in FIG. 2H, the second region may be an entrance of the first core hole (i.e., the first region or the cut-out non-articular surface) or may lie in a region between the uncut portion of the first non-articular surface and the entrance of the first core hole. The first auxiliary hole may then be drilled toward the interior of the first core hole (e.g., to enlarge the diameter of an entrance, interior, and/or exit of the first core hole) or the other uncut portions of the first bone.

The cutting may be continued in the first bone to extend the first core hole to the first articular surface, and a core portion of the first articular surface may then be removed through or cut out around the first core hole, thereby providing the first bone with a first core opening (FIGS. 2C, 2E, 2F, 2J, and 2K). Similarly, the cutting may be continued in the first bone to extend the first auxiliary hole toward the first non-articular surface (FIGS. 2E, 2F, and 2G), toward the first articular surface (FIGS. 2I, and 2J), toward the interior of the first core hole (FIGS. 2C, 2F, and 2G), and toward other regions of the first bone. An auxiliary portion of the first articular surface may also be drilled through or cut out around the first auxiliary hole, thereby providing the first bone with a first auxiliary opening. The first core and auxiliary holes may be spaced apart (FIG. 2C) or arranged to communicate with each other (FIGS. 2E to 2G, 2I, and 2J). The first core and auxiliary holes may also be arranged at angles (FIGS. 2C, 2E to 2G, 2I, and 2J) or parallel with each other (not shown). As described in greater detail below, it will be appreciated by persons of skill in the art that the general techniques described for forming auxiliary holes from the first core hole also may be used to resect all or a portion of the bone end.

Once at least the core opening is provided in the first bone as shown in FIGS. 2C, 2E to 2G, and 2I to 2K, the articular surfaces of the first and/or second bones or the anatomical structures of the joint may be treated by pharmaceutical agents, fluid agents, and/or surgical tools. If desired, one or more implants may be inserted and secured to such holes. The cut-out portions of the first articular surface and/or bone core may be reimplanted. After the first core and/or auxiliary holes are provided in the first bone as exemplified in any of FIGS. 2A to 2K, if there is a need to treat the second bone or to place an implant therein, the second bone may be cut according to any of the configurations shown in FIGS. 2L to 2R. FIGS. 2L through 2R correspond to various transosseous core approaches where the first bone is provided with the first core hole traversing the entire length of the first bone and optionally with first auxiliary holes.

In FIG. 2L, the articular surface of the second bone ("second articular surface") is drilled through or cut out in its first region which is disposed substantially opposite to the first core opening, thereby providing the second bone with a second core opening. A core portion of the second bone is then cut out further into its interior until it reaches a desirable depth, thereby providing the second bone with a second core hole (designated as "CH2" in the figures) configured to receive an implant. The second core hole is generally cut out in line with the first core hole (e.g., FIGS. 2L, 2N, and 2P to 2R) so that both core holes define a substantially straight pathway for the tools or implants such as magnetic arrays, orthopedic prostheses, pharmaceutical or fluid agent delivery systems, mechanical superstructures, and/or surgical prostheses. However, as shown in FIGS. 2M and 2O, the second core hole may be cut in an angle with respect to the first core hole by using, e.g., an angled cutting tool which will be discussed in greater below (see FIGS. 14A and 14B).

One or more auxiliary holes also may be created in a second region of the second bone ("second auxiliary hole" referred to as "AH2" in the figures). In FIG. 2N, the second region is an entrance of the second core hole (i.e., the second region or the cut-out articular surface of the second bone) from which the second auxiliary hole may be extended toward the uncut portion of the second bone such as the second non-articular surface or interior thereof. As shown in FIGS. 2P and 2Q, the second region may also be an interior of the second core hole, and the second auxiliary hole may be cut toward the uncut portion of the second bone. In the alternative, as shown in FIG. 2O, the second region may lie in a region between the uncut portion of the second articular surface and the entrance of the second core hole. The second auxiliary hole may be drilled toward the interior of the second core hole or the other uncut portions of the second bone. Furthermore, as in FIGS. 2Q and 2R, the second region may be an uncut portion of the non-articular surface of the second bone ("second non-articular surface") from which the second auxiliary hole may be drilled toward an interior of the second core hole or toward the uncut portion of the second bone. An auxiliary portion of the second articular surface may also be drilled through or cut out around the second auxiliary hole, thereby providing the second bone with a second auxiliary opening. The second core and auxiliary holes may be spaced apart (FIG. 2R) or arranged to communicate with each other (FIGS. 2N to 2Q). The second core hole and auxiliary holes may also be arranged at angles (FIGS. 2N to 2R) or parallel with each other (not shown). Once again, utilizing the techniques herein, the second bone may be resected through the first core hole.

Once the core and/or auxiliary openings are provided in the second bone, the second articular surface or the anatomical structures of the joint may be treated and, if preferred, the implant may be inserted into and secured to the holes. The cut-out portions of the second articular surface and/or bone core may also be reimplanted if appropriate.

Before beginning a transosseous core procedure according to the invention, the patient is properly positioned (e.g., seated or inclined with or without relative traction for treating the shoulder joint) to provide access to and proper alignment of the bones of the joint to be operated on. Careful placement of the patient on the operating table and positioning of the joint to be operated on will facilitate the sequence of steps to be performed. For example, various holding devices may be movably or fixedly attached to a stable operation table. Specific parts of a patient may be linked to the holding device and/or operating table by utilizing surface anatomy and through conventional fixation methods employing, e.g., calipers, pins, clamps with inflatable bladders, and the like. Other holding means or their modifications may be used in the transosseous core approach so long as they allow the joint bones to be readily movable and positioned without excessive restriction. For example, the holding device is preferably constructed to allow the joint to be mobile in flexion/extension, abduction/adduction, rotation, and/or three-dimensional translation. Such holding devices may be directed toward translatory support during specific phases of the surgical procedures or may be configured to provide continued and sustained positioning that may be occasionally readjusted. Additional positioning features may also be incorporated to the holding devices for precise adjustment thereof so that the surgeon may manipulate each degree of freedom separately to achieve the final desired position of the joint to be operated on.

In order to further illustrate the present invention, an exemplary embodiment is described using a model of a large joint, in particular, the shoulder joint. A person of ordinary skill in the art will recognize that the principles, techniques and devices disclosed herein may also be readily adapted to be used in other joints without departing from the scope of the present invention.

Figure 3:
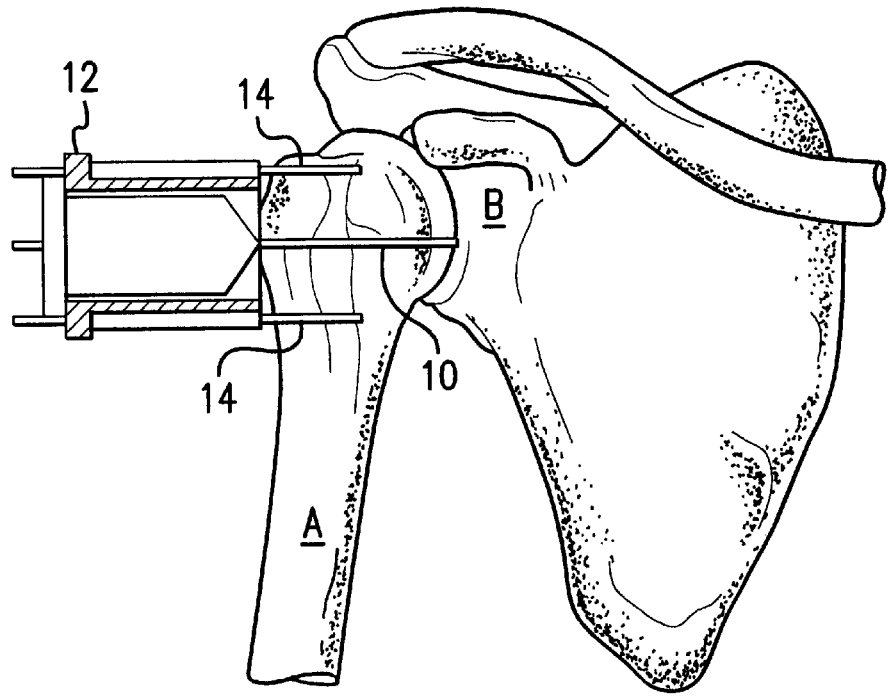
FIG. 3 is a schematic cross-sectional view of an initial step of the transosseous core approach and exemplary instrumentation for treating a shoulder joint according to the present invention.

After being properly positioned on the operating table, the patient is prepared and draped in the normal sterile fashion. As shown in FIG. 3, bone "A" is a humerus, while bone "B" is a scapula or, more particularly, the glenoid thereof. Bone "A" is also generally the "first transversed bone," "first bone" or "more accessible bone," while bone "B" is the "second adjacent bone," "second bone" or "less accessible bone."

Preoperatively, the surgeon utilizes X-rays CAT scan or MRI to view the bone and surrounding tissues to be operated, e.g., a humerus, humeral head, and glenoid for the shoulder joint. Based on these images, the surgeon makes exact measurements of the joint configurations, e.g., such as relative retroversions of the humeral head with respect to epicondyles of the humerus. The surgeon also determines an optimum drill depth for the humeral head and/or glenoid, size of the core hole(s), core depth, size of the implant such as core and auxiliary implants, axial rods, trans-prostheses, etc. The size and angle of retroversion may also be confirmed between the glenoid neck and the glenoid itself. By utilizing various positioning features of a holding device, the surgeon identifies an optimal position of the humeral head and glenoid for treatment, e.g., a position of 30° abduction and 30° external rotation in case of the shoulder joint. An AP radiograph is taken once the patient is positioned to verify relative orientation of the bones. Based on the MRI images, the surgeon may also check the surrounding anatomical structures such as vasculature, supracapular nerves, muscles, ligaments, and other soft tissues disposed adjacent or surrounding the joint.

After the patient's upper shoulder and chest are prepared and draped, a small incision or stab wound is made, e.g., along the mid-lateral vertical direction, about one centimeter inferior to the lateral border of the acromion, and dissection is performed from subcutaneous tissues to the deltoid. A suture is placed in the inferior limit of the separation of the deltoid muscle in order to prevent undesirable dissection which may endanger the axilliary nerve. The deltoid is then divided in the direction of fibers and a cylindrical retractor may be placed thereon to expose a pre-selected portion of the first bone (e.g., non-articular surface such as the lateral humerus). Referring again to FIG. 3, a guide wire or pin 10 is then inserted through a region inferior to the suprascapular attachment. Guide wire 10 is then drilled into the first bone to an appropriate depth at appropriate angles with respect to the axes of the first transverse bone on the X-Y and X-Z planes (e.g., axial, sagittal, coronal, and/or lateral directions) so that it is centered in the head. For example, depending on the objective of the intervention, guide wire 10 may be placed into interior of the first bone, through the first articular surface of the first bone, and into the interior of the second bone through the second articular surface of the second bone. The position of guide wire 10 may be confirmed using at least two orthogonal interoperative radiographic views.

As shown in FIG. 3, guide assembly 12 is placed over guide wire 10 and inserted through the wound while repositioning blood vessels, nerves, ligaments, muscles, tendons or other soft tissues surrounding the joint so that they are not trapped inside guide assembly 12. If necessary, blood vessels or sensory branches of nerves may be divided as well. Following placement of guide assembly 12, additional pins 14 may be placed through pin guide 25 so as to hold guide assembly 12 in place. Guide wire 10 and pins 14 are preferably made of a material such as stainless steel having appropriate mechanical strength and may be shaped and sized to be easily inserted through the anatomical structures surrounding the joint.

Guide assembly 12 generally includes an obturator and a drill guide, where the obturator is preferably movably disposed inside the drill guide. FIGS. 4A to 4C are views of an exemplary guide assembly 12 according to the present invention, where FIG. 4A is a side view of an exemplary obturator 16 and where FIGS. 4B and 4C are a side view and a top view of a matching drill guide 22, respectively.

Obturator 16 generally includes a cylindrical body 17 and defines an internal bore 18 which is formed along a central longitudinal axis thereof and shaped and sized to receive guide wire 10 therethrough. A distal portion of obturator 16 is truncated to form a distal tip 19 which may be pointed enough to be inserted around the anatomical structures surrounding the joint, but not sharp enough to cut, penetrate and/or otherwise destroy such, thereby clearing the site of insertion from unnecessary anatomical structures such as the soft tissues. A circular flange 20 is also attached to a proximal portion of obturator 16 and arranged to have a diameter greater than that of obturator body 17.

Drill guide 22 generally includes an annular cylindrical body 23 which couples with an annular flange 24 at its distal portion. Annular guide body 23 is generally arranged to receive cylindrical body 17 of obturator 16 therethrough. Thus, annular guide body 23 is sized to have an inner diameter which is slightly greater than the outer diameter of obturator body 17. Annular guide flange 24 also has an inner diameter greater than that of obturator body 17 but less than the outer diameter of circular obturator flange 20. Therefore, when obturator 16 is inserted into drill guide 22, cylindrical annular body 23 allows longitudinal translation of obturator 16 up to a position where annular guide flange 24 abuts a distal step 21 of obturator flange 20 and prevents further translation of obturator 16. Annular guide body 23 and/or guide flange 24 also define multiple longitudinal bores 25 around circumference thereof which are configured to receive additional positioning or anchoring pins 14 therethrough. For example, drill guide 22 exemplified in FIGS. 4B and 4C includes four identical bores 25 distributed at every 90° around annular guide flange 24 through an entire length of annular guide body 23.

Figure 5:
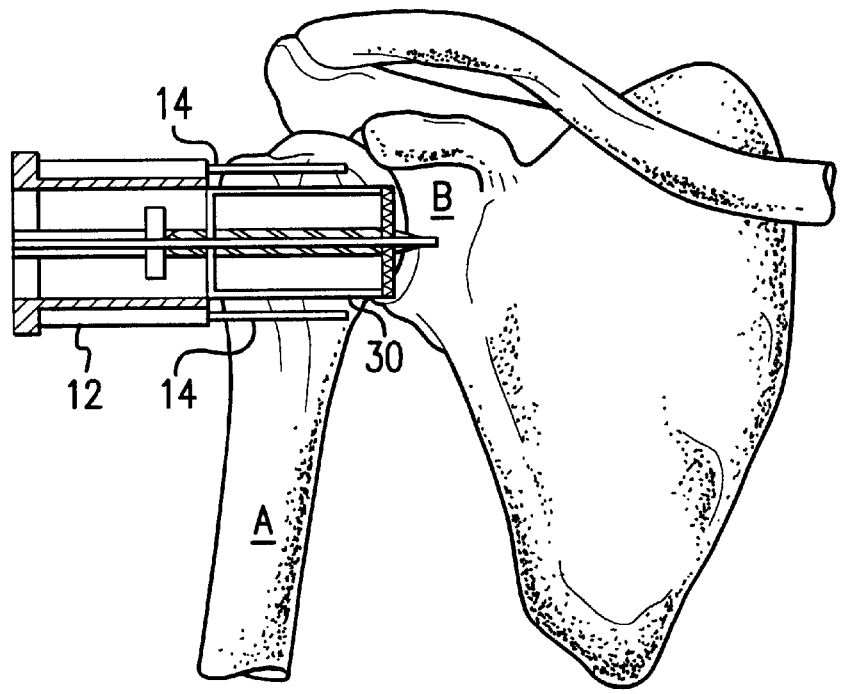
FIG. 5 is a schematic cross-sectional view illustrating a core cutting step and exemplary instrumentation therefor according to the present invention.

As shown in FIG. 5, once drill guide 22 is properly positioned and secured in place, obturator 16 is removed from drill guide 22 retrogradely and core cutter 30 is inserted therein to cut and remove a core from the first bone, i.e., the humeral head. As will be explained in greater detail below, the first core hole may continue through the first articular surface of the first bone by cutting out a first core portion of the first articular surface. Various implants may be disposed in the first core hole, e.g., to replace or augment one or entire portion of contour of the first articular surface of the first bone (i.e., resurfacing implants) or to generate or manipulate mechanical interaction between the first articular surface of the first bone and the opposing second articular surface of the second bone (i.e., non-resurfacing implants). The first core hole may also be used to provide access for repairing soft tissues, repairing, removing or replacing cartilage, arthroplasty, removing or repairing bones or reattaching the glenoid labrum, and the like. Examples of resurfacing and non-resurfacing implants are disclosed in detail in co-pending U.S. patent application Ser. No. 09/594,356, entitled "Magnetic Array Implant" ("the '356 application") which is incorporated by reference herein in its entirety.

The diameter of the first core hole is dictated by many factors including, e.g., the size of the first bone, configuration of the first bone in its transverse position, shape and size of a particular implant to be inserted and secured to the surrounding anatomical structures, and the like. Therefore, core cutter 30 is generally specifically designed for use with implants having specific configurations. The depth to which the first core is cut into the first bone also depends upon the factors described above. In procedures where the first core hole is to receive a joint resurfacing implant, the first core hole preferably continues through the first articular surface of the first bone by cutting out a first core portion of the first articular surface. However, in situations where a non-resurfacing implant is to be used, the first core hole may stop appreciably or immediately before the first articular surface of the first bone. Other implants and prostheses may also be employed. Magnetic or non-magnetic resurfacing implants may be used to form a portion of the first articular surface. When the first bone is structurally compromised and, therefore, includes multiple bone portions, non-magnetic prosthesis or magnetic assemblies may provide mechanical integrity to the first bone. In addition, a drug or agent delivery system may be inserted into the bone to perform either pharmaceutical or rheological interventions in the joint. For example, a pharmaceutical or rheological agent may be injected directly from the agent delivery system or introduced via a carrier medium for inducing pharmacological intervention for treating the bones, their articular surfaces or other anatomical structures surrounding the joint. Steroids, antibiotics, antiviral pharmaceuticals, radioactive isotopes, and chemotherapeutics are typical examples of such pharmaceutical agents. A fluid agent such as hyluronic acid-based liquids may also be injected directly to the joint so as to provide lubrication between the articular surfaces, and/or other viscous liquids may be injected to absorb shocks transmitted through the joint bones.

Figure 6:
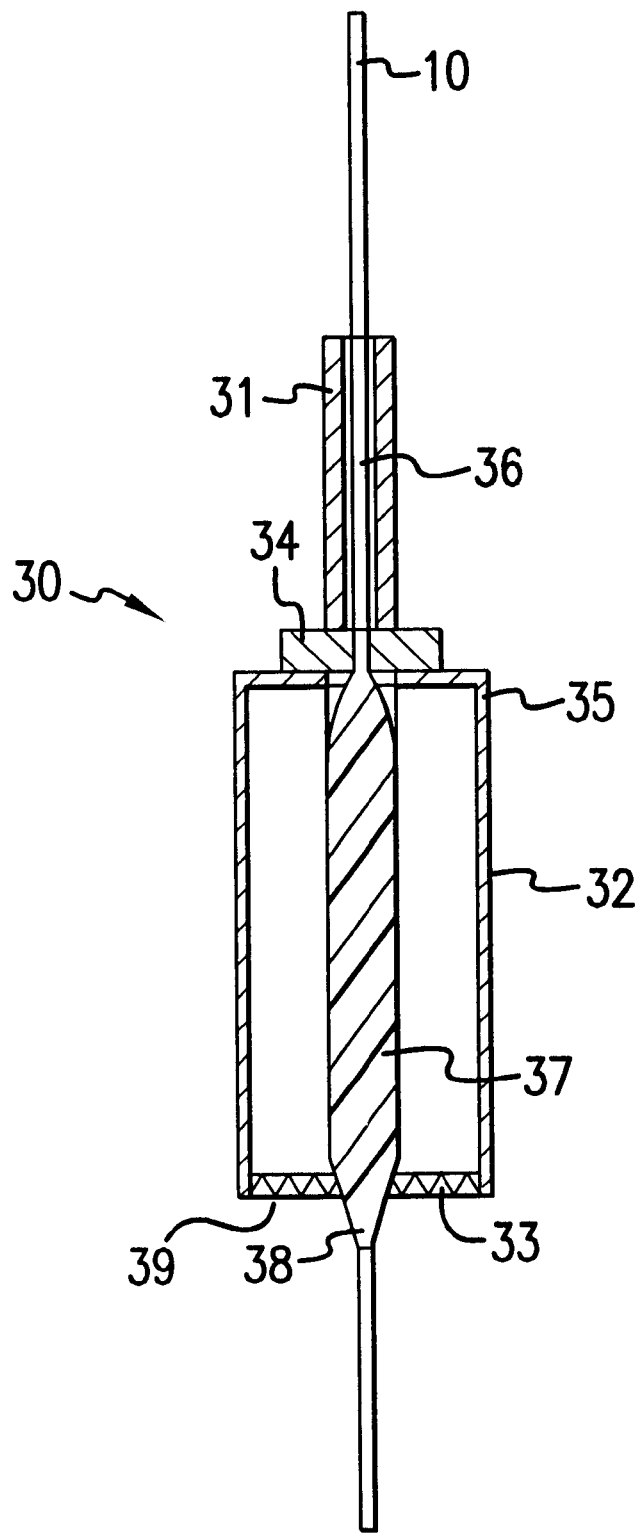
FIG. 6 is a cross-sectional view of an exemplary core cutter according to the present invention.

Although the first hole of the first bone may be drilled through by a drill bit and the bone material and/or cartilage separated from the bone may be removed through a proximal portion of drill guide 22, a hole saw is preferably used to provide a bone core that may be preserved and reimplanted back at the first core hole after repairing, replacing or treating the joint. Therefore, the transosseous core approach of the present invention preferably employs an annular core cutter as shown in FIG. 6 for preserving at least a portion of the first bone core. Core cutter 30 typically includes an elongated cylindrical shaft 31, annular cutting element 32 with multiple cutting teeth 33 disposed at a distal portion thereof, and connector 34 for mechanically coupling annular cutting element 32 to shaft 31. Shaft 31 is arranged to couple with an oscillation or rotation device (not shown) so that oscillatory or rotational motion of the device is delivered to cutting element 32 through connector 34. Cutting element 32 is typically shaped as an annular cylinder which is open at its distal end 39 and which includes a circular base 35 at its proximal end. Shaft 31, connector 34, and base 35 are preferably arranged to define a bore 36 formed along a longitudinal axis of core cutter 30 and arranged to receive guide wire 10 therethrough so that core cutter 30 is guided therealong. Annular cutting element 32 may be made of high-strength material so that thickness of circumferential wall and cutting teeth 33 can be maintained at their minimum. Such an embodiment minimizes loss of bone during the cutting process.

An auxiliary drill shaft 37 may be provided inside annular cutting element 32 to provide mechanical strength to core cutter 30 for maintaining its shape and/or integrity as well as to provide a central hole for discharging debris and/or supplying irrigation fluid during the cutting process. The length of auxiliary drill shaft 37 may vary depending on the need, e.g., shorter than that of annular cutting element 32 or longer so that a distal tip 38 of auxiliary drill shaft 37 slightly extends out of distal end 39 of annular cutting element 32. Distal tip 38 of auxiliary drill shaft 37 may be pointed to facilitate anchoring of core cutter 30 during the cutting process. Auxiliary drill shaft 37 may also be provided with cutting edges or teeth which may facilitate drilling a center portion of the first bone core.

Similar to the case of drill guide 22, the optimal shape and size of core cutter 30 are a matter of selection of those skilled in the art, and generally determined by various factors including, e.g., the size of the first bone, configuration of the first bone in the transverse position, size of the resurfacing and/or non-resurfacing implant to be used, and the like. In the exemplary embodiment of the shoulder joint, a core cutter for providing the first core hole of one inch in diameter may include an annular cutting element of about two inches in length, about one inch in diameter, and about 0.2 mm to 1.5 mm in wall thickness. Each cutting tooth may have a width of about 0.5 mm or less. The auxiliary drill shaft may have a diameter ranging from about 2 mm to 20 mm, e.g., more preferably about 6 mm to 7 mm. It is appreciated that the above configuration of the core cutter may be adjusted by persons skilled in the art, e.g., according to a desired diameter and depth of the first core hole, shape and size of the implant to be used, and the like. After reaching a desired depth, core cutter 30 is removed from drill guide 22 along with the first bone core at least a portion of which may be preserved for later reimplantation thereof into the first core hole.

Figure 7:
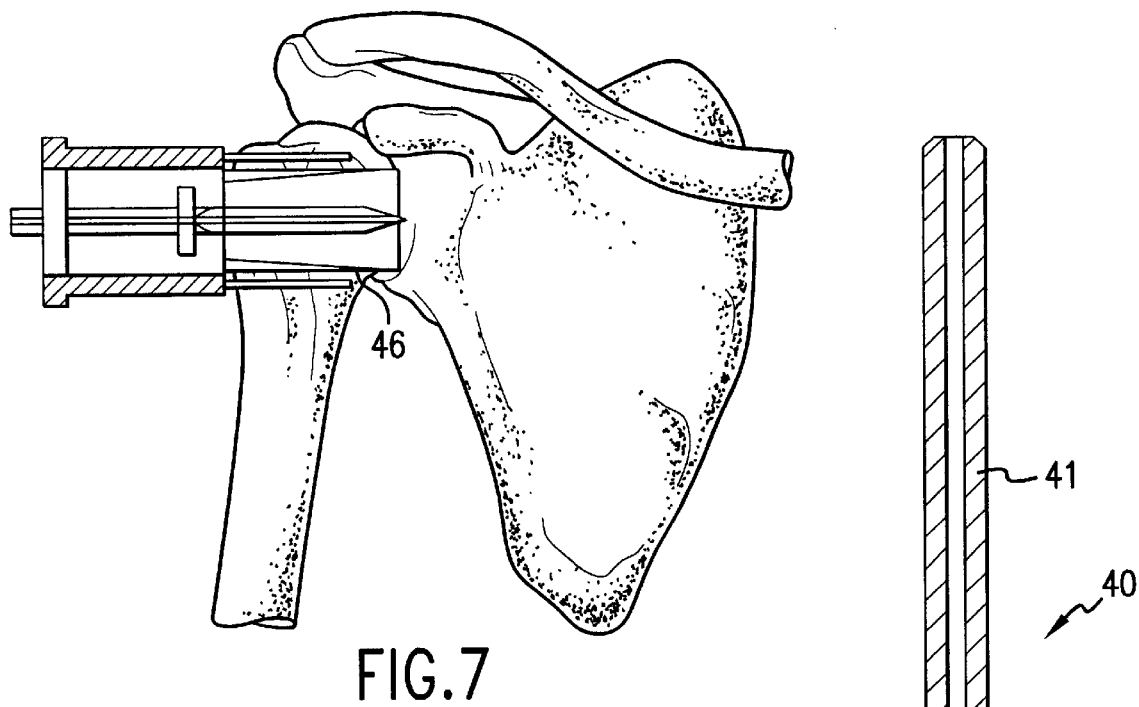
FIG. 7 is a schematic cross-sectional view illustrating a cartilage punching step and exemplary instrumentation therefor according to the present invention.

If the cartilage surface is to be reimplanted, after removing core cutter 30, a cartilage punch 40 is inserted through drill guide 22 as shown in FIG. 7. Cartilage punch 40 may be driven, oscillated or rotated to cut out a core portion of the first articular surface of the first bone and to provide the first core opening to the first bone. If preferred, the previous core cutting step may be terminated at a certain distance from the first articular surface such that at least a minimum thickness of the first bone is attached to the cartilage to preserve its mechanical integrity and physiological viability.

Figure 8:
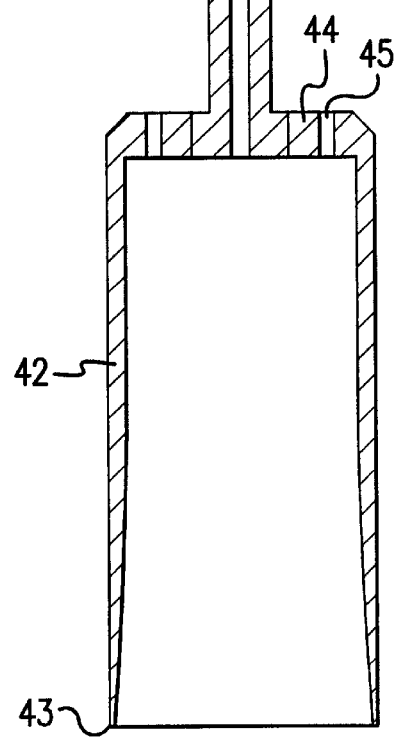
FIG. 8 is a cross-sectional view of an exemplary cartilage punch according to the present invention.

If the cartilage is damaged and/or non-functional, it may be drilled away by drill bits and discarded. Alternatively, a cartilage may be carefully incised, preserved, and reimplanted back at the first articular surface after repairing, replacing or treating the joint. However, because the cartilage is generally thin and sometimes inseparable from the residual bone attached thereto, a complex of the cartilage and bone ("cartilage-bone autograft" or simply "cartilage" hereinafter). As shown in FIG. 8, cartilage punch 40 is preferably designed to minimize the damage to the removed cartilage (or cartilage-bone autograft) to the extent possible. Cartilage punch 40 resembles core cutter 30 in many respects, e.g., including an elongated shaft 41, a blade 42 with a circular cutting edge 43 disposed at a distal portion thereof, and a connector 44 for mechanically coupling annular punch blade 42 to shaft 41. However, circular cutting edge 43 of cartilage punch 40 preferably has a thickness which may be substantially less than core cutting teeth 33 so that the portion of cartilage lost during the punching process may be minimized. An exemplary range of the thickness of cutting edge 43 is from about 0.2 mm to 1.0 mm, e.g., about 0.3 mm. In addition, blade 42 and cutting edge 43 are preferably made of high-strength material so that the first bone attached to the cartilage may be punched out and removed with the first articular surface thereby. In general, an upper limit of the diameter of annular blade 42 may be determined by a maximum diameter of the cut-out portion of the articular surface that would present negligible or minimal chance of damaging or interfering with other joint structures, e.g., in the range of up to few inches, preferably about 0.5" to 1.5". When the cartilage-bone complex is cut out using cutting blade 42 having the foregoing dimensions, the portion of the cartilage lost during the cutting process approximately amounts to 12 mm$^2$. The cut-out portion of the first articular surface or cartilage-bone autograft tends to be tightly fit around cutting edge 43 and, therefore, may pose difficulty in harvesting it without inflicting damages thereon. Accordingly, an opening 45 may be provided to connector 44 to allow a push rod to be inserted and to push the cut-out articular surface out of cutting edge 43. Alternatively, shaft 41 may be arranged to be pulled out of connector 44 and the push rod may be inserted therethrough.

Figure 9A:
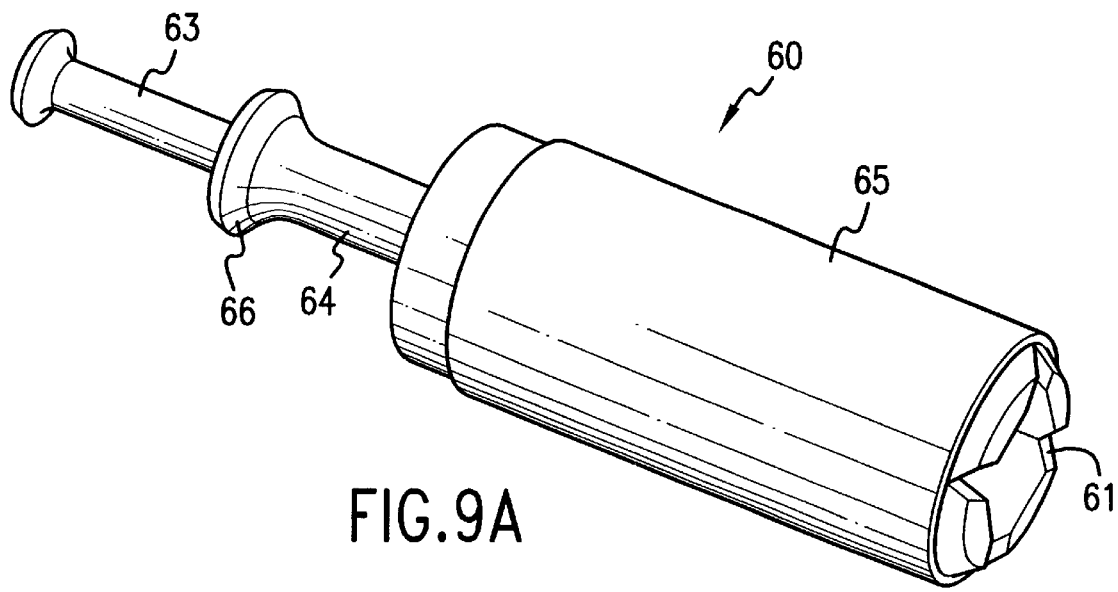
FIGS. 9A and 9B are perspective views of an exemplary hemostasis device according to the present invention.
Figure 9B:
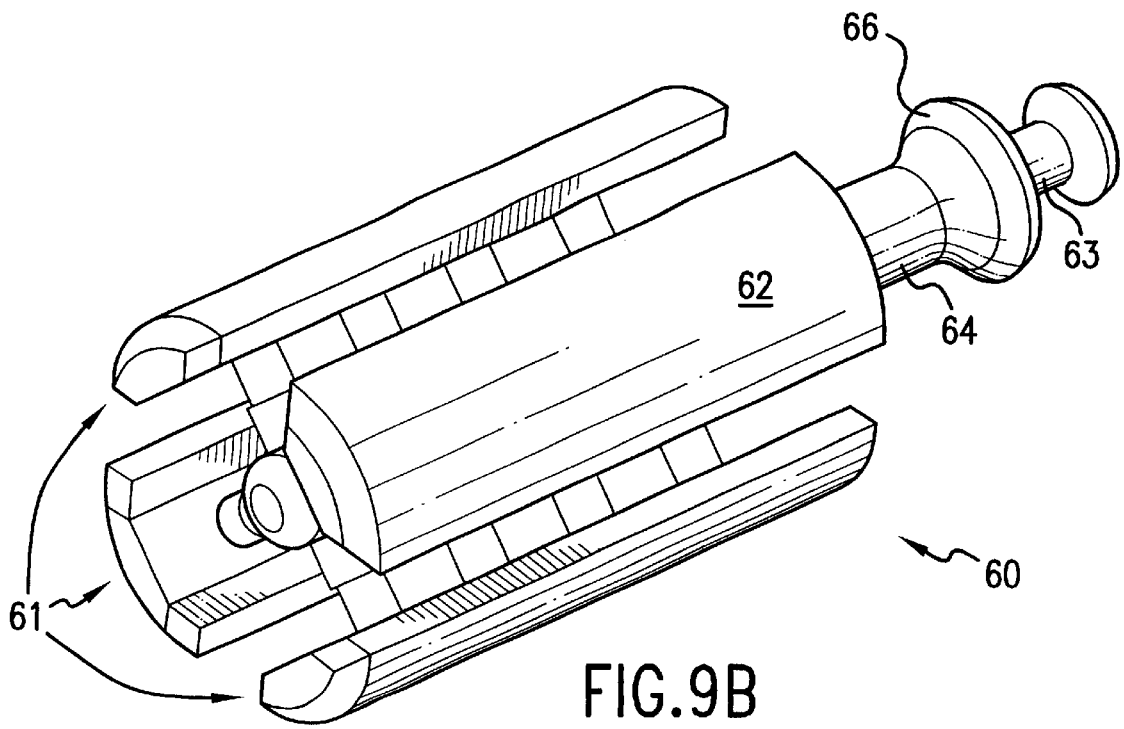

In some procedures, hemostasis of a bleeding bone (e.g., from the bone core hole) may be required. Hemostasis can be accomplished according to standard methods to reduce bone bleeding or by using hemostasis device 60 according to the present invention. As shown in FIGS. 9A and 9D, hemostasis device 60 according to the present invention includes an expansion element 61, a handle 63, a support 64, and hemostatic agent 65. In particular, FIG. 9A shows hemostasis device 60 in its retracted position. In this embodiment hemostatic agent 65 comprises beeswax shaped as an annular sleeve. As best seen in FIG. 9B, expansion element 61 comprises multiple elongated side members 62 each of which is movably coupled with shaft 64. Expansion element 61 is arranged to expand and retract in a radial direction between the expanded position and the retracted position by radial displacement of side members 62. Support 64 is generally a hollow cylinder with multiple radial arms and forms a grip 66 at its proximal end for ease of handling and operation. Handle 63 is movably inserted through a bore of support 64. Hemostatic agent 65 is shaped and sized to be placed over expansion element 61 and mounted thereon.

In operation, expansion element 61 is moved to its retracted position and covered by hemostatic agent 65. Hemostasis device 60 is inserted through drill guide 22, and positioned adjacent to surfaces of the bone hole where bleeding is to be stopped. While maintaining the position of hemostatic device 60, an operator pushes handle 63 distally so that expansion element 61 is triggered to expand in the radial direction toward its expanded position. Hemostatic agent 65 then deforms and stretches with expanding expansion element 61 until it contacts the surfaces of the bleeding bone. After the beeswax contacts the bleeding surfaces, the operator may further push handle 63 so that side members 62 of expansion element 61 firmly spread hemostatic agent 65 over the bleeding surfaces and/or smear the agent into pores of the bleeding surfaces. After obtaining hemostasis, the operator releases handle 63 so that the retraction mechanism pulls in side members 62 of expansion element 61 to the retracted position. Hemostasis device 60 is then pulled back through drill guide 22.

Persons of ordinary skill in the art may devise any number of suitable expansion mechanisms for such hemostasis devices. Examples of such expansion mechanism may include, but not limited to, a spring release mechanism, a screw based mechanism, and their functional equivalents which may include manual, pneumatic or hydraulic engaging or disengaging mechanisms. Various hemostatic materials may be used in the hemostasis device as long as such materials can directly or indirectly induce hemostasis by, e.g., physically and/or pharmacologically blocking bleeding from the bone holes or physiologically constricting blood flow therefrom. Examples of the hemostatic materials may include, but not limited to, beeswax, a mixture of gelfoam and thrombin, and the like. Hemostatic materials may also be provided in various forms, e.g., as a cylindrical bar, single trough or multiple rounds.

Once adequate hemostasis is achieved, the surgeon may treat the joint or the second bone. Alternatively, the surgeon may insert, through drill guide 22, one or more resurfacing or non-resurfacing implants as previously discussed. The above procedures may be repeated for insertion of additional implants to complete appropriate joint treatment as described, e.g., in the co-pending '356 application.

Additional instrumentation (i.e., a specifically adapted endoscope lens or camera with appropriate illumination devices) can be utilized to allow the surgeon to visualize the opposing articular surface of the second adjacent bone and allow preparation of the second bone (if necessary) to receive appropriate components. Additional entry sites may be provided if additional implants are to be used, e.g., as described in the co-pending '356 application. Such implants may be implanted by traditional techniques or the transosseous core approach described herein above. These steps equally apply to the resurfacing and non-resurfacing implants as well as the modules thereof.

The transosseous core approach of the present invention may also be completed after removing the first articular surface of the first bone and placing resurfacing and/or non-resurfacing implants in the first core hole. For example, when the cartilage of the first bone needs to be removed and replaced by autograft, allograft, zenograft, and/or other replacements made of, e.g., metals, polymers, ceramics, etc., the cartilage may be punched out and such implants may be inserted at the cut-out portion of the cartilage to cover the cut-out opening of the first articular surface. The first bone core may then be reimplanted back at the first core hole, the first core hole closed (e.g., by the cut-out bone core may be harvested from the first and/or second bone) and the joint treatment may be terminated.

As discussed above, in situations where the joint treatment requires insertion of the resurfacing and/or non-resurfacing implants in the opposing, second articular surface or an interior of the second bone, the surgeon may continue with preparation of the second bone after hemostasis is achieved to a satisfactory degree. The transosseous core approach under such circumstances permits cutting of the second bone core hole(s) through the first bone core hole as described. Such approach may also be applied when a more-accessible bone of the joint is not the one to be treated, i.e., when a cartilage of the more-accessible bone is functionally operative, whereas an opposing cartilage of the less-accessible bone needs to be replaced or treated. After completing treatment of the cartilage of the less-accessible bone by securing the resurfacing and/or non-resurfacing implants thereto, the cartilage and/or the bone core of the more- and/or less-accessible bone may be reimplanted at the articular surfaces and/or in the core holes to minimize post-surgical injury to the functionally operative joint.

Figure 10:
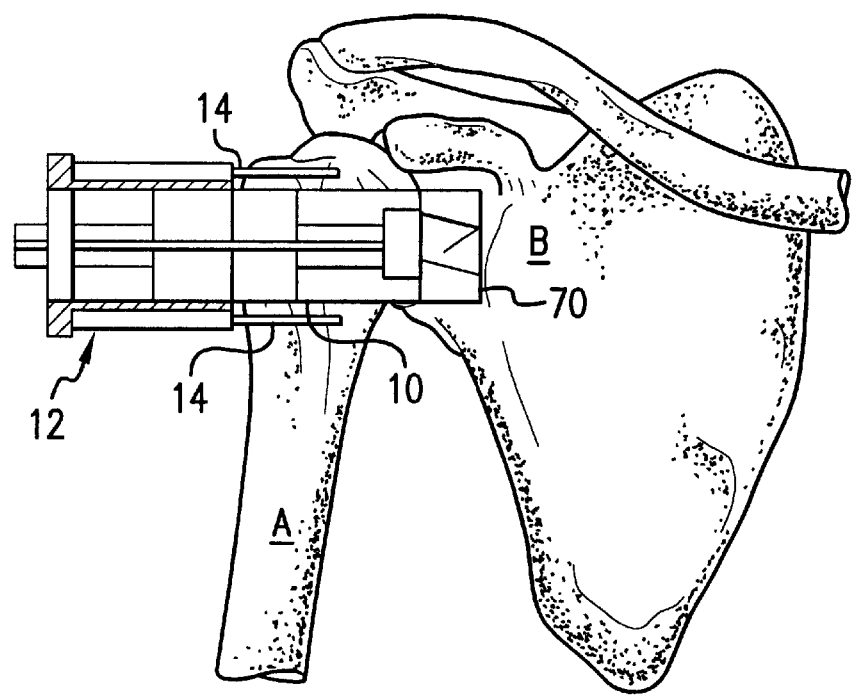
FIG. 10 is a schematic cross-sectional view illustrating a bone-reaming step and exemplary instrumentation therefor according to the present invention.

FIG. 10 illustrates opening the pathway in the second bone according to the present invention. Reamer 70 is preferably inserted over guide wire 10 through drill guide 22 to cut a second core hole in the second bone. Once again, the cutting element (e.g., reamer 70) is preferably shaped and sized with the implants to be inserted in the second bone hole such that the cutting element has a cross-section complementary to that of the implants to be implanted in the second bone. Alternatively, core cutter 30 may be again used to provide a second core hole. Furthermore, when the second bone core is not to be reimplanted or when the glenoid implant is affixed to the second bone by conventional screws or adhesive components, other cutting tools known in the art may also be used.

Once the second core hole is properly cut in the second bone, the resurfacing and/or non-resurfacing implant described above may be introduced into the second bone through the first and second core holes. Preferably, at least the major components for resurfacing, non-resurfacing or joint-replacing implants are placed through the pathway created in the first bone. Accordingly, such implants preferably have dimensions allowing them to pass through the first core hole. Alternatively, as will be described in greater below, multiple implant modules may be inserted through the first core hole and assembled in situ so that the assembled implant modules (i.e., "implant assembly") have one or more final dimensions greater than those of the first core hole.

Figure 11:
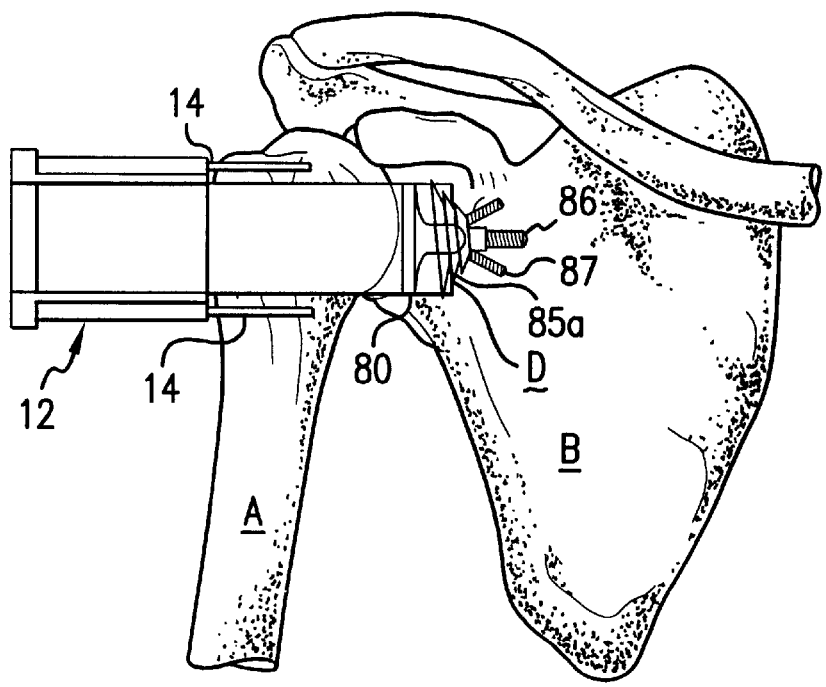
FIG. 11 is a schematic cross-sectional view illustrating the step of implanting an exemplary glenoid prosthesis according to the present invention.

FIG. 11 illustrates placement of an exemplary second core implant (i.e., glenoid implant 80) in the second bone according to the present invention. In the figure, the first bone and second bone are denoted as "A" and "B," respectively, and the first and second core holes as "C" and "D," respectively.

Figure 12A:
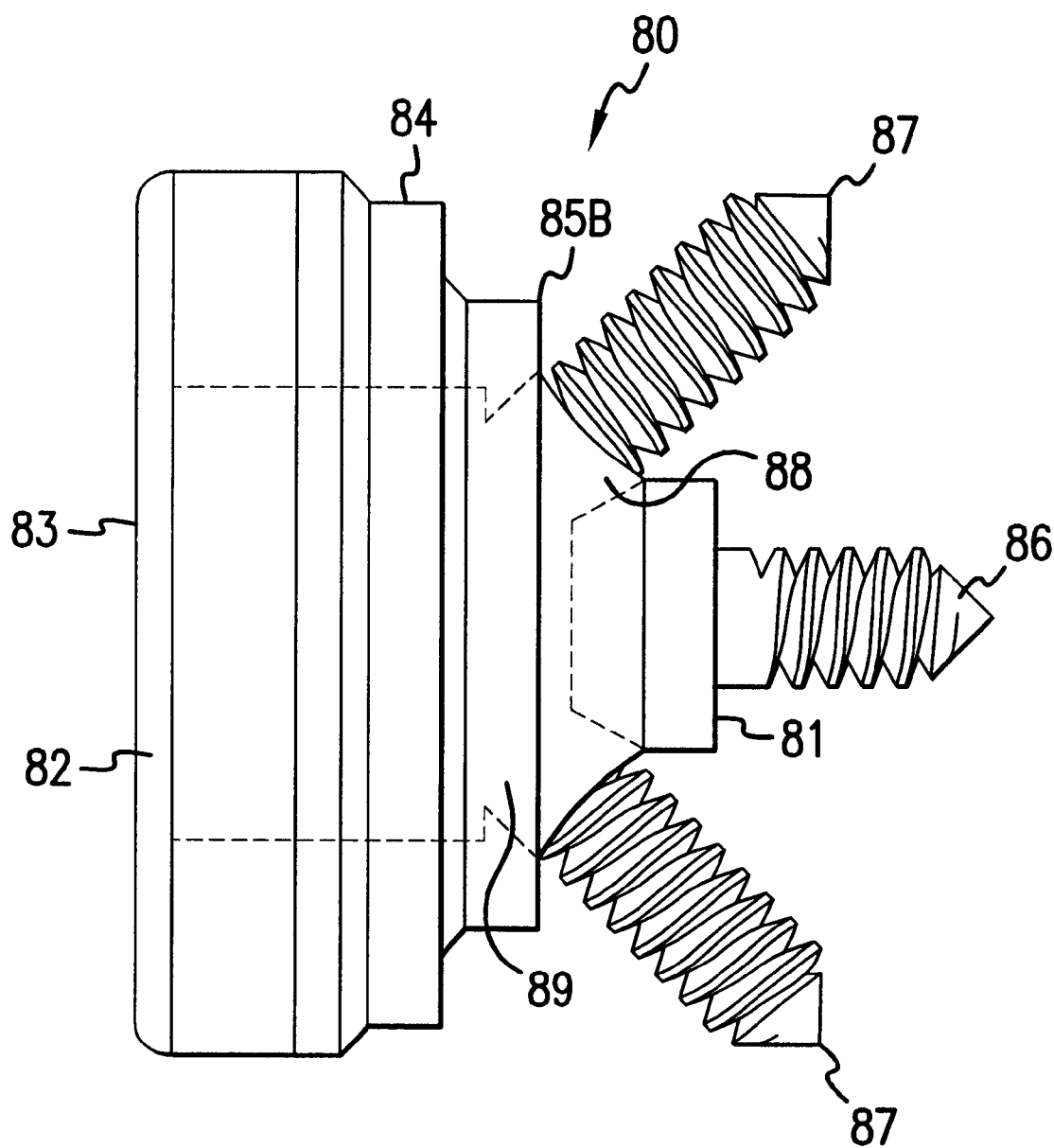
FIG. 12A is a side view of an exemplary glenoid implant as shown in FIG. 11.

One embodiment of glenoid implant 80, illustrated in FIG. 12A, generally includes structures for treating the joint and for securing itself to the second bone. For example, glenoid implant 80 includes a treatment layer 82 which is secured to a main body 84 thereof. If glenoid implant 80 is to be used as a resurfacing implant, bearing surface 83 of treatment layer 82 is preferably contoured so that, upon implantation, it can replace at least a portion of the second articular surface of the second bone. Bearing surface 83 can be preferably made of ultra-high molecular-weight polyethylene. Other suitable polymers, metals, ceramics or materials that may reduce friction and wear and which yield little or no wear debris under the calculated load maybe used. However, when glenoid implant 80 is used as a non-resurfacing implant, treatment layer 82 may include an array of magnets configured to generate desirable magnetic fields therearound (e.g. as discussed in the co-pending '356 application). Alternatively, treatment layer 82 and/or body 84 may include a pharmaceutical delivery mechanism which may directly or indirectly induce desired pharmacological response in the joint. Glenoid implant 80 also includes anchoring structures such as interference fit surface 85B (e.g., a step cut or press fit) that extends from body 84 and terminates as an anchoring screw 86 at its distal end. Alternatively, the main body of the implant may incorporate a tapered screw thread 85A as shown in FIG. 11. Anchoring screw 86 generally serves as a guiding element for initially positioning glenoid implant 80 at a desired position of the second core hole in a desirable orientation, whereas interference fit surfaces 85B or tapered thread 85A provides a greater contact area with the second bone and, therefore, helps to secure glenoid implant 80 to the second bone. In order to obtain desired orientation of glenoid implant 80 and to prevent unintended rotation thereof, additional anchoring elements may be provided as well. For example, the embodiment of FIG. 12A includes a pair of side screws 87 protruding from interference surfaces 85B (or tapered screw 85A). Side screws 87 are inserted through cavities and bores provided in body 84.

Figure 12B:
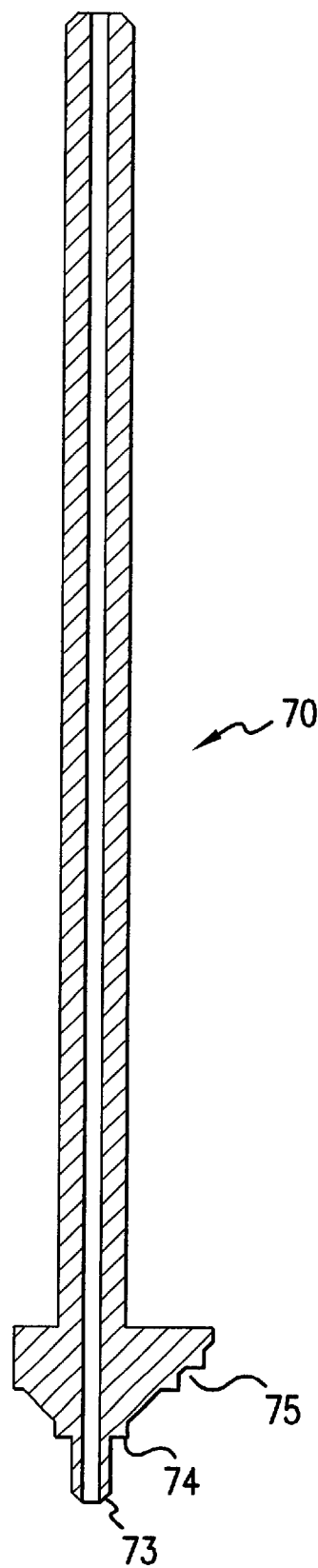
FIG. 12B is a cross-sectional view of a reamer according to the present invention.

For proper implantation of glenoid implant 80 with interference surfaces 85B, the second core hole is preferably shaped, such as by reaming, to match the profile of the implant. FIG. 12B shows an exemplary reamer 70 for this purpose. Tip 73 creates a small bore in the bone for anchoring screw 86. Step 74 provides a flat surface on the bone abutting a distal step 81 of glenoid implant 80. An angled side 75 of reamer 70 offsets interference surfaces 85B or tapered screw 85A, etc., to facilitate implantation of glenoidal implant 80. At the same time, reamer 70 ensures an adequate amount of the second bone to facilitate fixation of glenoidal implant 80.

In operation, glenoid implant 80 is inserted through the first core hole and its opening, and then placed at a location in the second core hole with or without treatment layer 82 attached thereto. Interference fit surfaces 86B are anchored into the second bone by rotating entire glenoid implant 80 or by rotating distal screw 86. When treatment layer 82 is not attached to body 84 of glenoid implant 80, side screws 87 may be directly inserted through bores 88 in the implant and anchored into the second bone. Treatment layer 82 is then inserted through the first and second core holes and secured to body 84 of glenoid implant 80 at desirable orientation. Alternatively, treatment layer 82 may be provided with access holes (not shown) through which side screws 87 may be inserted and secured to the second bone. In this embodiment, side screws 87 may be retained inside body 84 and/or tapered screw 85A with their distal tips retracted therein during the insertion of glenoid implant 80. After properly positioning and orienting glenoid implant 80, side screws 87 are secured into the second bone.

If desired, reamer 70 may be arranged to cut the second core hole having a shape and/or size different from those of the first core hole. For example, reamer 70 with a smaller cutting area may be used to provide the second core hole smaller than the first core hole. This embodiment may generally be preferred when the second articular surface to be treated is smaller than the first core opening cut out in the first articular surface of the first bone or when the larger first core hole has to be made in the first bone due to various anatomical and/or instrumental limitations.

Figure 12C:
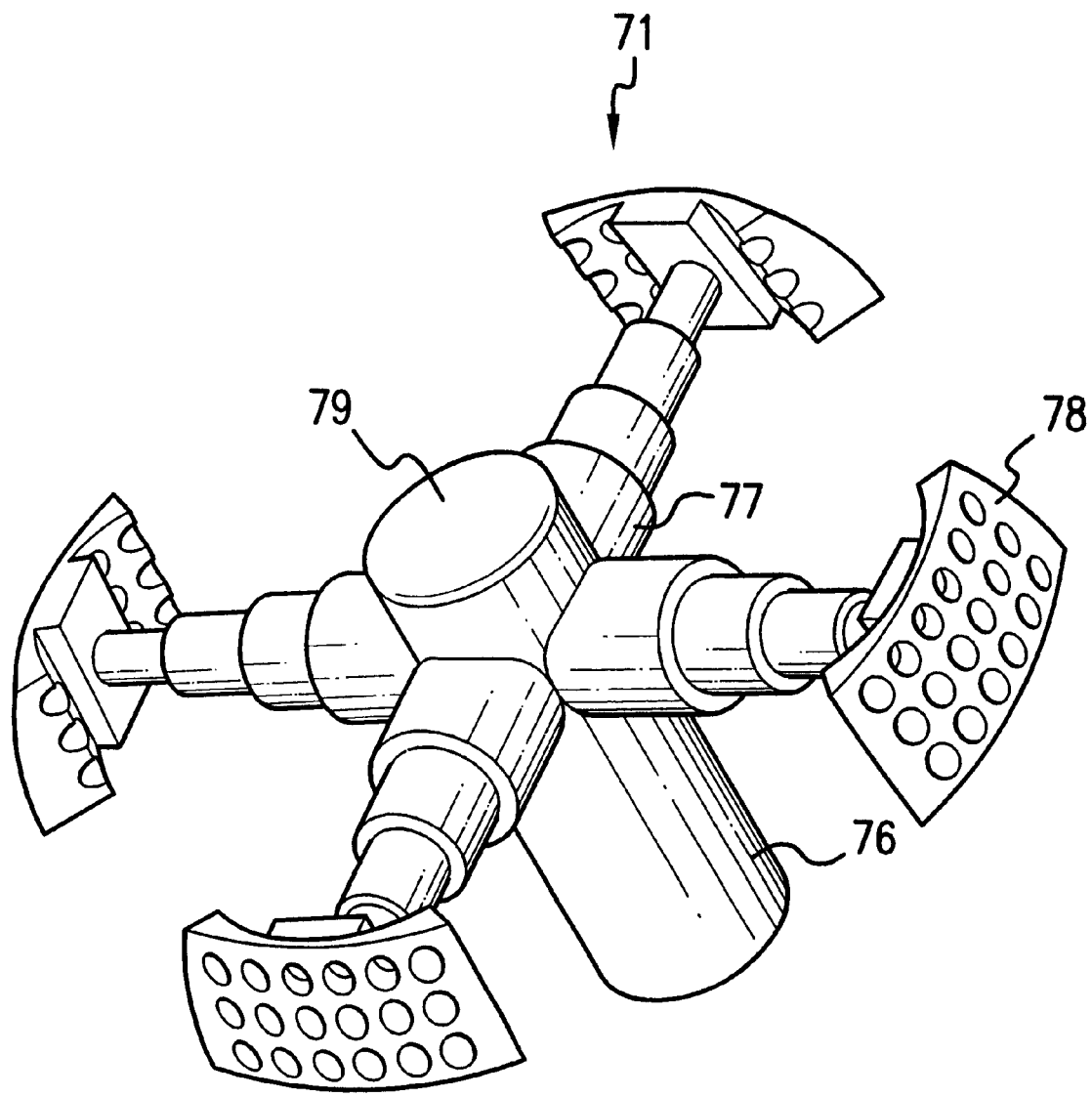
FIG. 12C is a perspective view of an expandable reamer according to the invention.

In one alternative, a larger core hole may be cut in the second bone by using a specially arranged cutting device incorporating an expandable mechanism capable of providing a cutting area having a diameter greater than that of a main shaft of the cutting device. This embodiment is generally preferred when the second articular surface of the second bone to be treated is larger than the first core opening of the first bone, when the first core hole has to be made smaller because of the anatomical and/or instrumental limitations or when the larger core hole has to be cut in the second bone due to the similar reasons. FIG. 12C is a schematic diagram of an exemplary expandable reamer according to the present invention.

Expandable reamer 71 typically includes a main shaft 76 and four extendable arms 77 each of which includes a cutting device 78 at its distal end. Extendable arms 77 move between a retracted position and an extended position. In its retracted position, arms 77 are retracted so that expandable reamer 71 as a diameter at least slightly less than the diameter of the first core hole to permit it to be inserted through the hole. In its expanded position, however, arms 77 extend distally so that the diameter of expandable reamer 71 increases beyond that of the first hole. Expandable reamer 71 may include a pointed retractable distal tip 79 to facilitate positioning thereof. Once again, expandable reamer 71 is preferably shaped and sized with the implants to be inserted in the second bone such that it may have a cross-section in its extended position matching or offset to that of the implants to be implanted in the second bone.

Figure 13A:
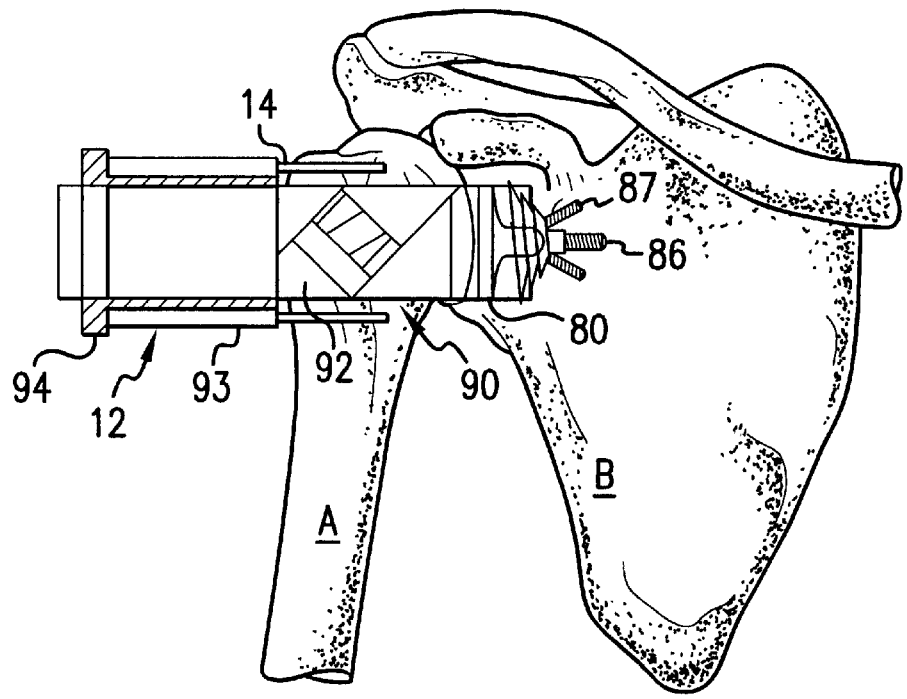
FIGS. 13A and 13B are schematic cross-sectional views illustrating the steps of providing exemplary auxiliary holes in the first bone and exemplary instrumentation therefor according to the present invention.
Figure 13B:
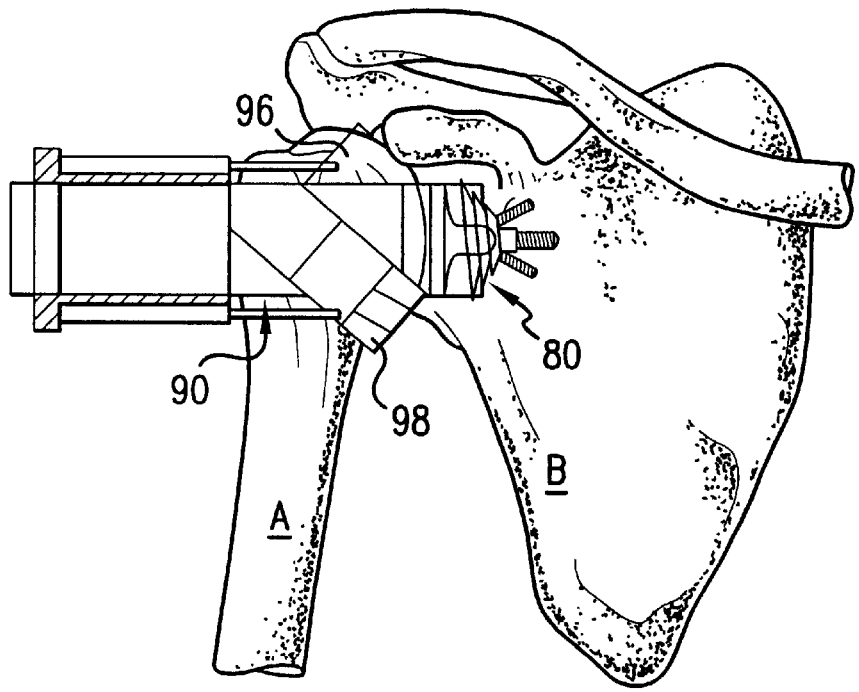

In particular procedures it may be necessary or desirable to remove an area of bone that is greater than the cross-sectional area of the bone core hole. This may be required, for example, to provide resurfacing over a full range of joint motion in some joints. Such a larger internal removal may be accomplished with an angled reamer such as illustrated in FIGS. 13A, B and 14A, B. As shown in FIG. 13A angled reamer 90 is positioned through guide assembly 12 to cut a superior or first auxiliary hole. After cutting the superior auxiliary hole 96, reamer 90 is rotated to position it for cutting an opposite, inferior or second auxiliary hole as shown in FIG. 13B.

Figure 14A:
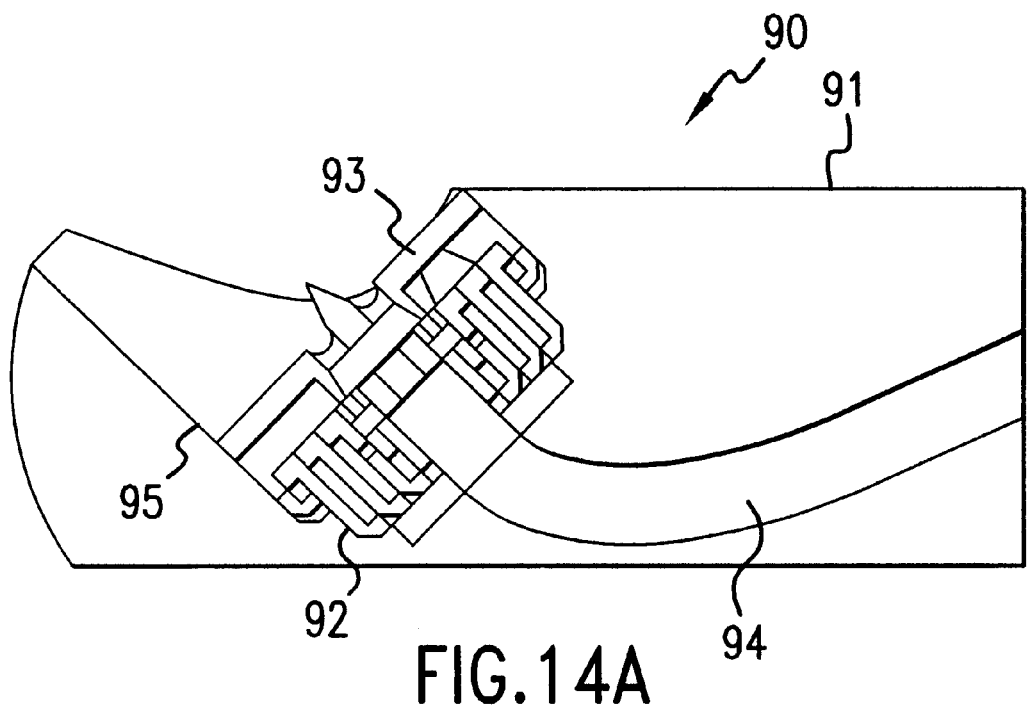
FIGS. 14A and 14B are cross-sectional views of an exemplary angled reamer suitable for providing auxiliary holes as shown in FIGS. 13A and 13B according to the present invention.
Figure 14B:
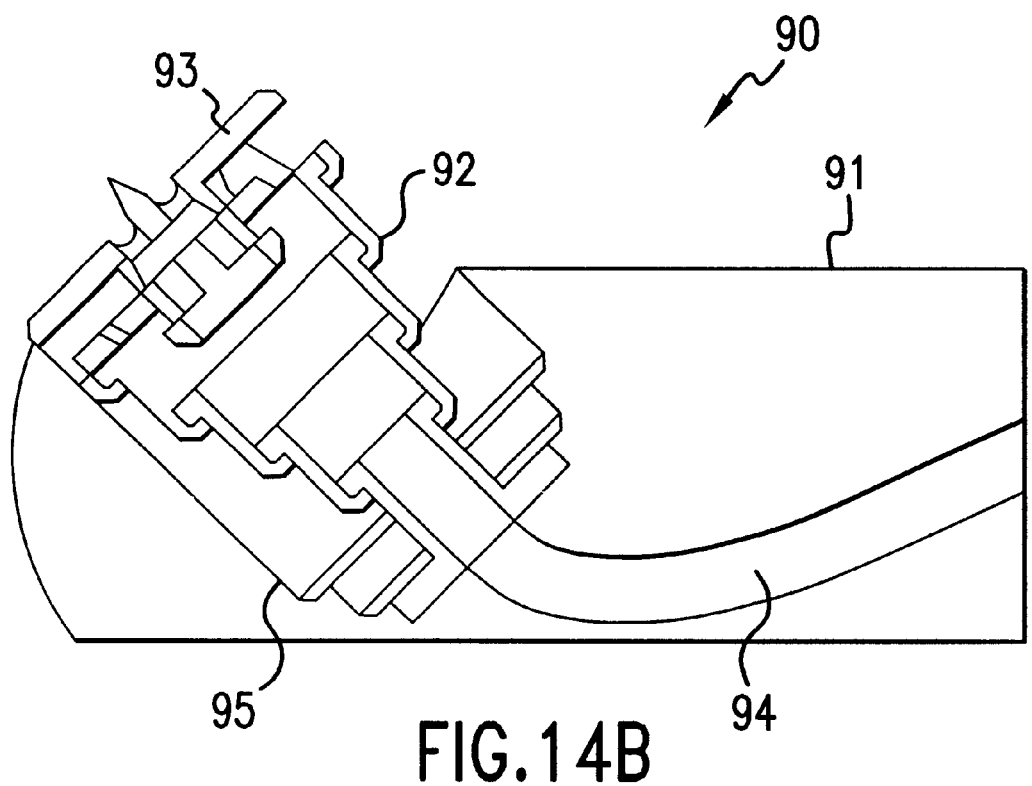

As illustrated in FIGS. 14A and 14B, one embodiment of angled reamer 90 according to the invention includes an annular cylindrical body 91 including therein extendable shaft 92, cutting element 93, and power transmission cable 94. Cutting element 93 is coupled to power transmission cable 94 and arranged to transmit rotational power generated by a power source (not shown) to cutting element 93. Body 91 includes a housing 95 arranged to receive and retain extendable shaft 92 therein. Cutting element 93 is disposed at a distal end of extendable shaft 92 and movably supported thereby. Extendable shaft 92 adjusts its length by moving between a retracted position (FIG. 14A) where cutting element 93 and shaft 92 are retained inside housing 95 and an extended position (FIG. 14B) where cutting element 93 extends out of housing 95 by a desirable distance.

In operation, extendable shaft 92 is pulled into its retracted position (FIG. 14A) so that an entire portion of extendable shaft 92 and cutting element 93 is retracted into housing 95. Angled reamer 90 is then inserted through drill guide 22, and positioned inside the first core hole at a desired depth and orientation with respect to the longitudinal axis of the first core hole. As shown in FIG. 14B, cutting element 93 is engaged and extendable shaft 92 gradually extends out of housing 95 toward its extended position, thereby forming an auxiliary hole by removing bone at the angle set by housing 95 supporting cutting element 93. After a first auxiliary hole is cut to a desired depth, cutting element 93 is disengaged and extendable shaft 92 is pulled in again to its retracted position along with cutting element 93. Angled reamer 90 is then may be rotated and reoriented, e.g., by 180° and, as shown in FIG. 13B, cutting element 93 is re-engaged, extendable shaft 92 is extended, and second and/or subsequent auxiliary holes are created.

Figure 15:
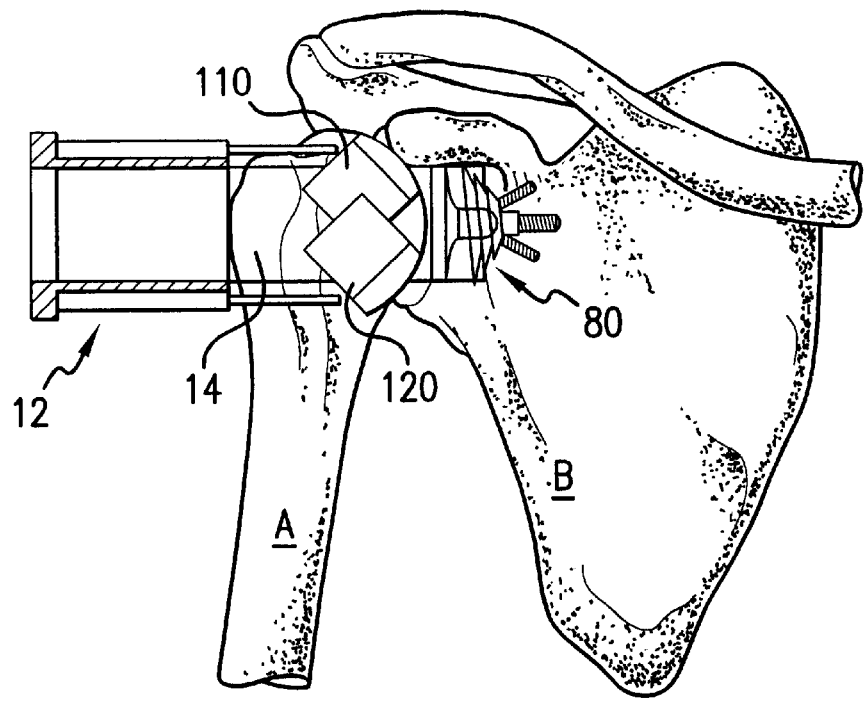
FIGS. 15 and 16 are schematic views illustrating an implant inserting step and exemplary instrumentation therefor according to the present invention.
Figure 16:
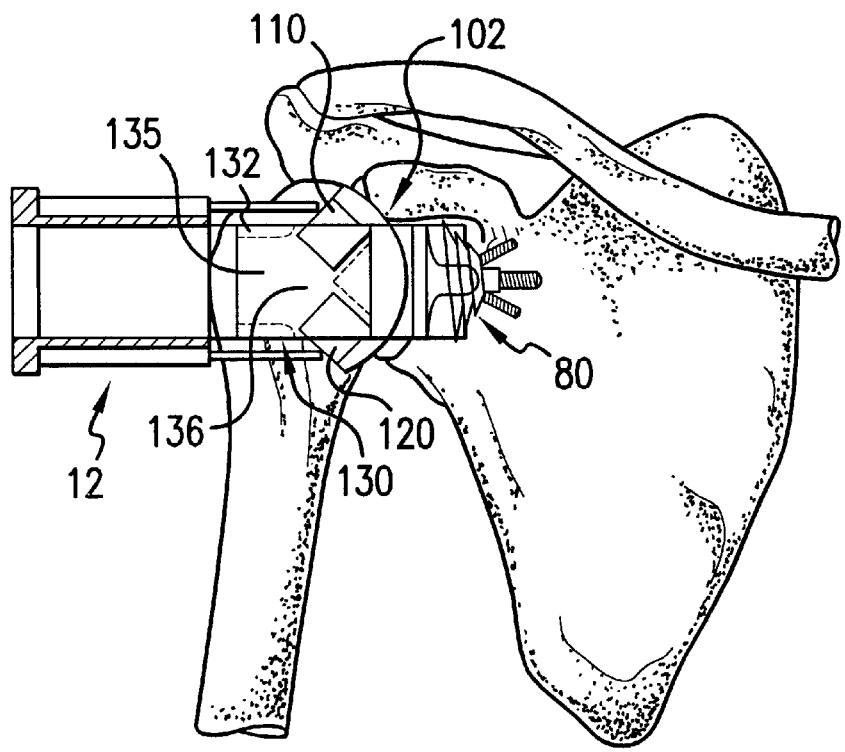

After auxiliary holes 96, 98 are drilled, core and auxiliary implants are inserted and secured as illustrated in FIGS. 15 and 16. First auxiliary implant (or implant module) 110 is first inserted through the first core hole and positioned in the first auxiliary hole 96, followed by positioning of an second auxiliary implant 120 in the second auxiliary hole 98. Positions of first and second implants 110, 120 may be checked radiographically so as to leave a preselected space therebetween. Core implant 130 is then inserted through the first core hole and disposed between superior and inferior implants 110, 120.

As explained, first core implant 130 and auxiliary implants 110, 120 are passed through the first core hole and then assembled in situ, thereby forming a first implant assembly having one or more dimensions greater than the first core hole. For this purpose, each of first implant modules 110, 120, 130 is provided with at least one coupling mechanism such as slots, screws, pins, magnets, or other coupling elements which may be devised by a person of ordinary skill in the art. Alternatively or additionally, each implant module 110, 120, 130 may be individually secured to the first bone, or a first implant module may be secured to the first bone, while the other two modules secured to the first module. FIGS. 17A to 17D illustrate exemplary embodiments of the implant assemblies according to the present invention.

Figure 17A:
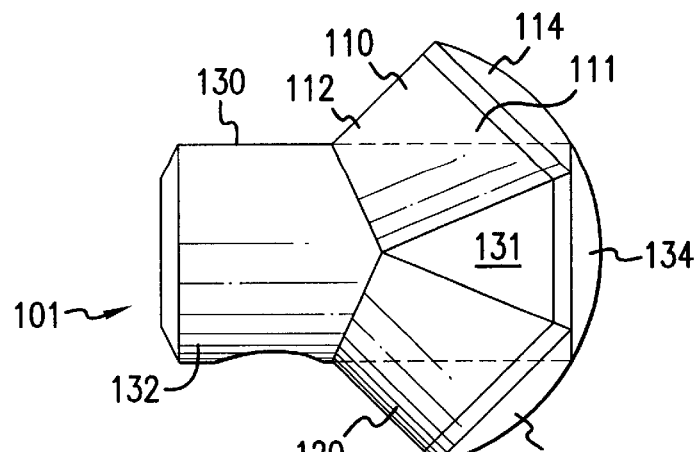
FIG. 17A is a side view of one embodiment of a joint-resurfacing implant according to the invention.

In FIG. 17A, an exemplary implant assembly 101 includes first implant 110, second implant 120, and cylindrical core implant 130, which is a substantially elongated cylinder having a diameter at least slightly less than the internal diameter of the cylindrical first core hole. Core implant 130 has distal end 131 and proximal end 132, and includes treatment layer 134 at its distal end, which is arranged to form a portion of the first articular surface, to interact with the second bone or to interact with an implant inserted in the second bone. First implant 110 is also shaped as a cylindrical rod but cut along an axis which connects one edge of its distal portion 111 and a diagonally opposing edge of its proximal portion 112 in such a way that a contoured inner surface of the truncated portion is concave to sung-fit an external surface of a side of main implant 130. Second implant 120 is also shaped as a cut cylinder so that its concave inner surface matches the external surface of an opposing side of main implant 130. Implants 110, 120 also include treatment layers 114, 124 which are arranged to perform the functions similar to treatment layer 134 of main implant 130. Treatment layers 114, 124 are also preferably contoured to form a substantially continuous contour with main implant 130. Therefore, when assembled together, implants 110, 120, 130 form a mechanical surface having a dimension substantially greater than the cross sectional area of the first core hole.

It will be appreciated that implant assembly 101 of FIG. 17A is functionally the same as, but configurationally different from, implant assembly 102 of FIG. 16. That is, in the embodiment of FIG. 16, cylindrical main implant 130 defines an angled cylindrical internal bore 135 commencing from proximal end 132, bifurcating into a pair of angled internal bores, and culminating in opposing openings 136 into which superior and inferior implants 110, 120 are inserted and secured. Therefore, implant assembly 102 of FIG. 16 is assembled by inserting main implant 130 into the first core hole, followed by inserting superior and inferior implants 110, 120 through internal bore 135 and securing such implants 110, 120 to main implant 130 by securing mechanisms as discussed below.

Figure 17B:
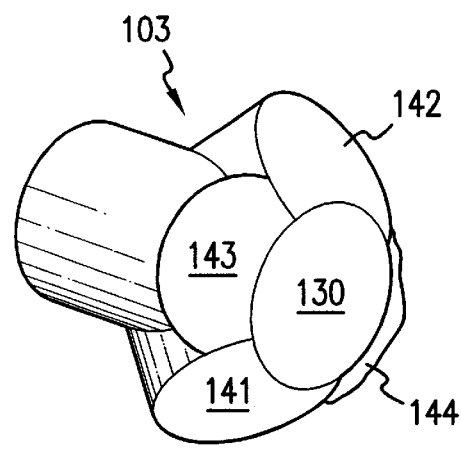
FIGS. 17B to 17D are perspective views of alternative embodiments of joint resurfacing implant assemblies according to the present invention.

FIG. 17B is a schematic view of another implant assembly 103 according to the present invention. Exemplary implant assembly 103 includes a pair of major implants (or implant modules) 141, 142 and another pair of minor implants (or implant modules) 143, 144 secured at four equi-spaced core and/or auxiliary holes provided around the first core hole in which main implant 130 is disposed. Each implant 130, 141–144 is arranged so that, when put together, a distal portion of implant assembly 103 forms a quadra-foil bearing surface which may form a portion of the first articular surface and which is substantially larger than the cross-sectional area of the first core hole. Each implant 130, 141–144 may also include at its distal end the treatment layer identical or similar to those discussed above. Similar to the previous implant assemblies and as shown in FIG. 17A, major and minor implants 141–144 may be first implanted and then secured to the peripheral surface of main implant 130 inserted subsequently thereafter (as shown in FIG. 17B). Alternatively, main implant 130 may be positioned in the first core hole, and major and minor implants 141–144 may be inserted through an internal bore and four equi-spaced openings of main implant 130 and subsequently secured to the first bone and/or main implant 130. Furthermore, each of main, major, and minor implants 130, 141–144 may be secured via a separate coupler (not shown) inserted through the first core hole so that the implant assembly maintains its configuration through the coupling force between the coupler and each implants 130, 141–144.

Figure 17C:
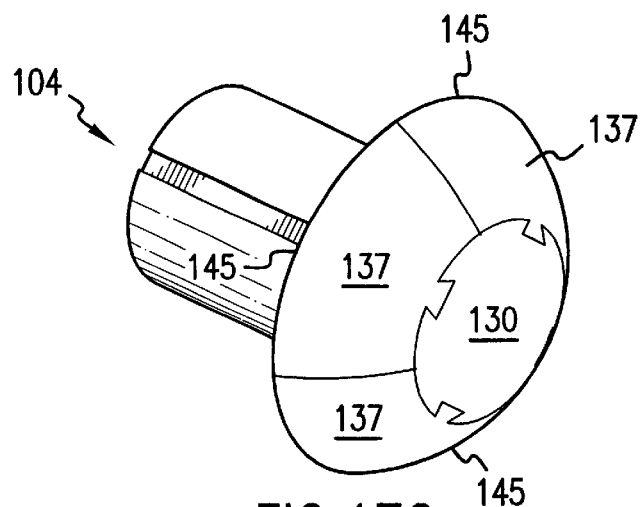

FIG. 17C is a perspective view of yet another exemplary implant assembly 104 according to the present invention. Similar to the embodiment of FIG. 17B, implant assembly 104 includes main implant 130. In this embodiment, four substantially identical auxiliary implants 145 are symmetrically disposed around implant 130. Treatment to surface 137 of each individual implant module preferably has a spherical shape such that when assembled together implants 130, 145 form an overall treatment surface for implant assembly 104 corresponding to a surface of a hemisphere or truncated hemisphere.

Figure 17D:
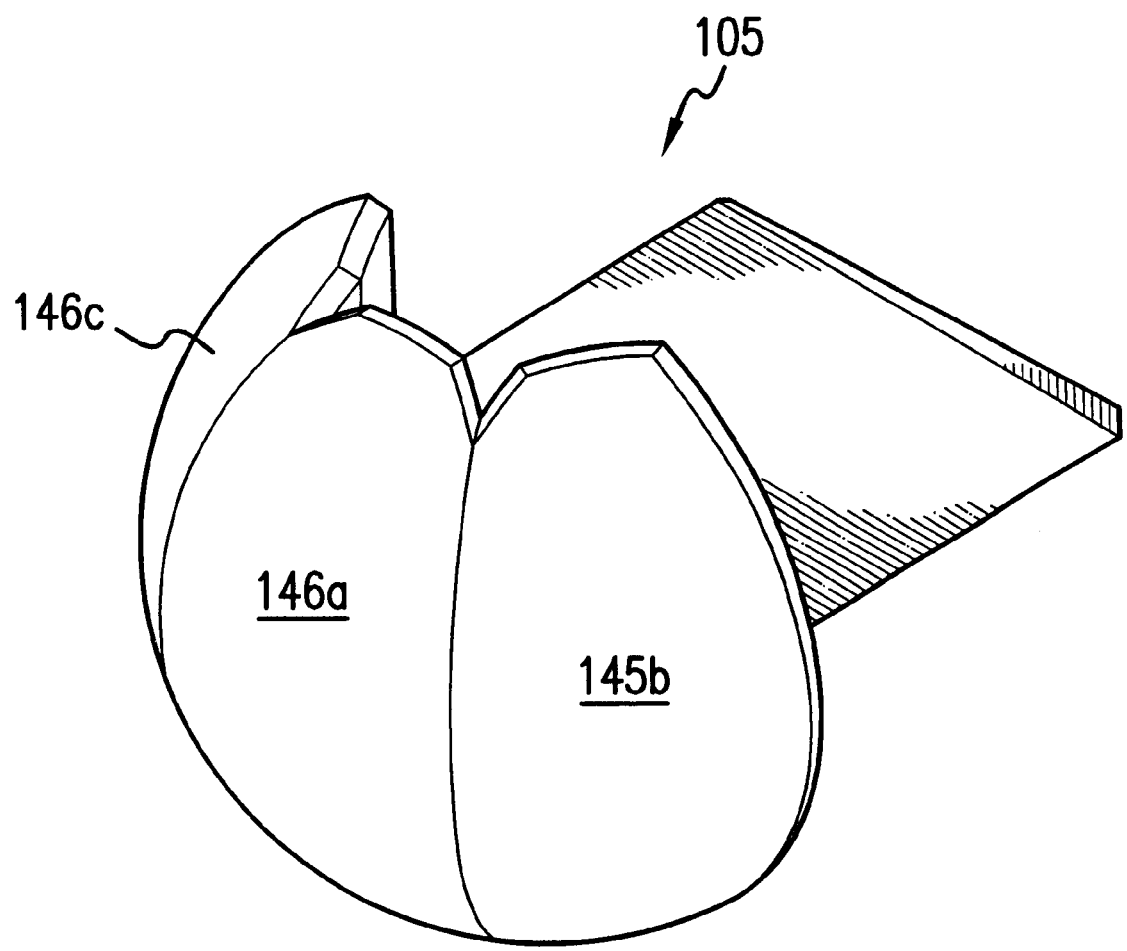

FIG. 17D is a perspective view of a further alternative implant assembly 105 according to the present invention. In this embodiment, implant assembly 105 includes three wedge-shaped implants (or implant modules) 146 which are substantially identical to each other and to be aligned side by side to form the assembly 105. Preferably central wedge 146*a* is designed with a specific side contour so that outer wedges 146*b* and 146*c* are mirror images of one another.

As discussed above, all auxiliary implants 110, 120, 141–146 preferably include at least one coupling mechanism so that they can couple to each other and/or with main implant 130 in situ to form the implant assemblies 101–105. In general, incorporating an appropriate coupling mechanism to the implant assemblies is a matter of selection of those skilled in the art. For example, each pair of adjoining implants may be arranged to have matching mechanical structures allowing mechanical coupling therebetween, such as a protrusion and a groove, a tongue and a groove (as illustrated in FIG. 17*c*), female and male threads, and the like. In addition, adjoining implants also may be coupled by screws, latches, latchets, and other conventional coupling articles. Alternatively, such implants may be coupled by magnetic forces as well.

Although auxiliary implants 110, 120, 141–146 may have general shapes or sizes similar or symmetrical to one other, the detailed geometry and/or properties thereof may be different. For example, auxiliary implants 110, 120, 141–146 may have the substantially identical shape and size but their treatment layers may have different contours to satisfy asymmetrical anatomical contours of the articular surface to be treated. When symmetric auxiliary implants 110, 120, 141–146 include magnetic arrays, they are preferably arranged to generate specific magnetic fields to meet range of motion of the joint bones. (See the copending '356 application, which is incorporated by reference).

Figure 18:
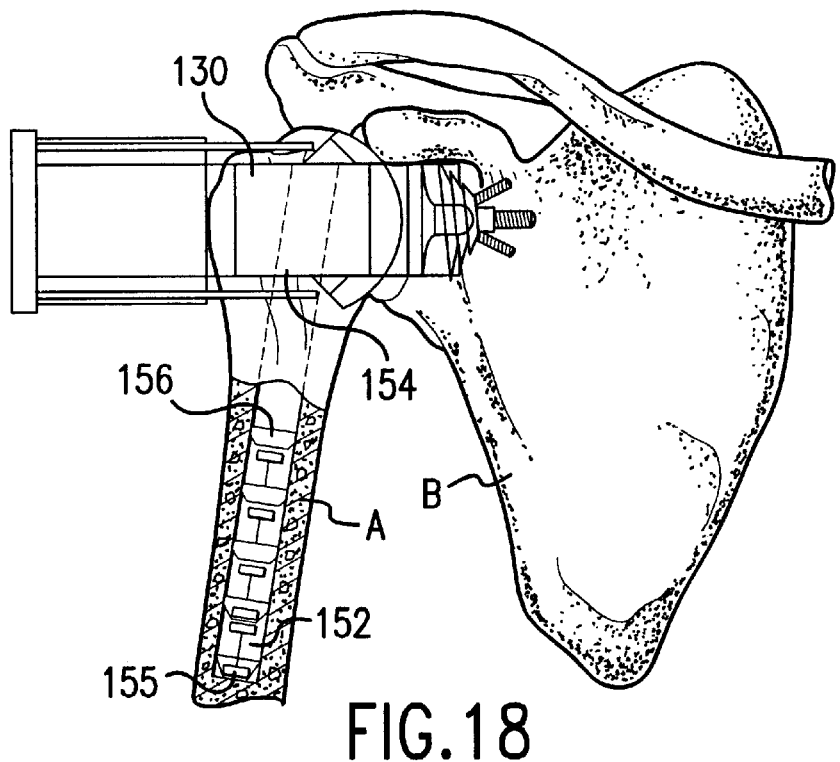
FIG. 18 is a schematic cross-sectional view illustrating an intramedullary canal and a component of an exemplary modular stem within the canal according to the present invention.
Figure 19:
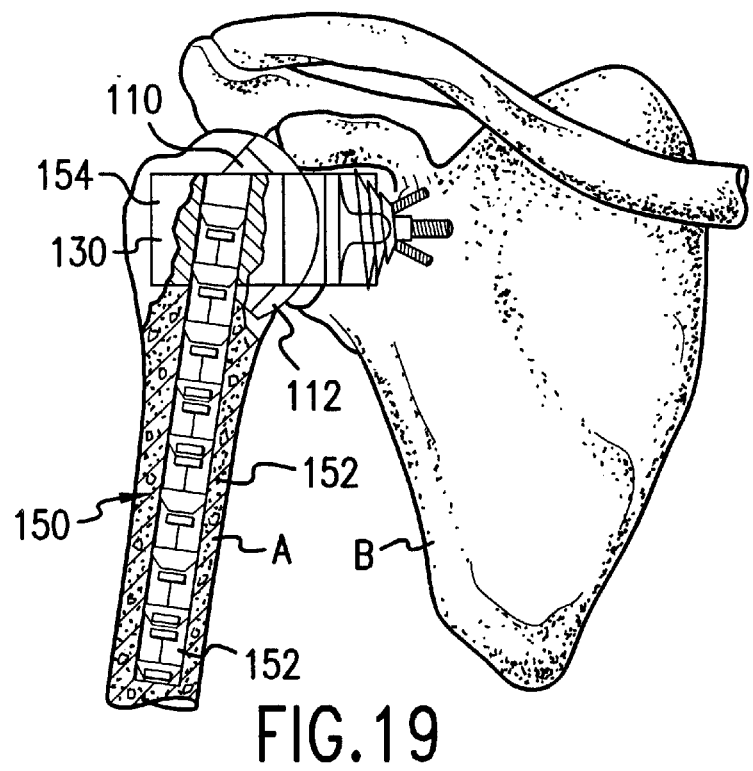
FIG. 19 is a schematic cross-sectional view illustrating an implant assembly of FIG. 18 for shoulder replacement according to an exemplary embodiment of the present invention.

Depending on the application, the type of implant and location, an intramedullary stem may be desirable to assist in stabilizing the implant. In the exemplary embodiment for the shoulder described herein, the humeral canal is reamed to the appropriate dimensions and shape using a specially adapted standard reamer with a flexible shaft. With the canal properly prepared, a modular stem may be inserted as shown in FIGS. 18 and 19. Modular stem 150 preferably is made up of a plurality of identical stem components 152 including initial and terminal components which may be constructed differently from the rest thereof. The stem components are inserted through an opening in the back side of core implant module 130 and dropped into the prepared canal through optional opening 154 or they can be placed prior to placing the implants. A connection means provided on the individual components causes them to lock together. For example, as shown in FIGS. 18 and 19, each stem component may be provided with tapered nose 155 and tapered open tail 156. The tapered nose and open tail are designed such that the nose is received in the tail with a slight interference fit. Stem components 152 also may be provided with internal magnets 156 that create a strong attractive force between the components and effectively lock them together. Magnets suitable for this purpose are described in greater detail in the co-pending '356 application, which is incorporated by reference. Other means for securing the stem components together include mechanical couplings such as screws or threaded stem components, tongue and groove, and keyed connections and the like.

As shown in FIG. 19 (shown with a portion of the wall of component 130 removed), once stem 150 is completely assembled, and after a further radiographic check to confirm positioning, the core that was removed from transversed bone A is replaced to close the bone hole. The drill guide retractor is removed. Standard procedures for closure of the wounds and hemostasis are completed following the completion of the implanting procedures.

Figure 20:
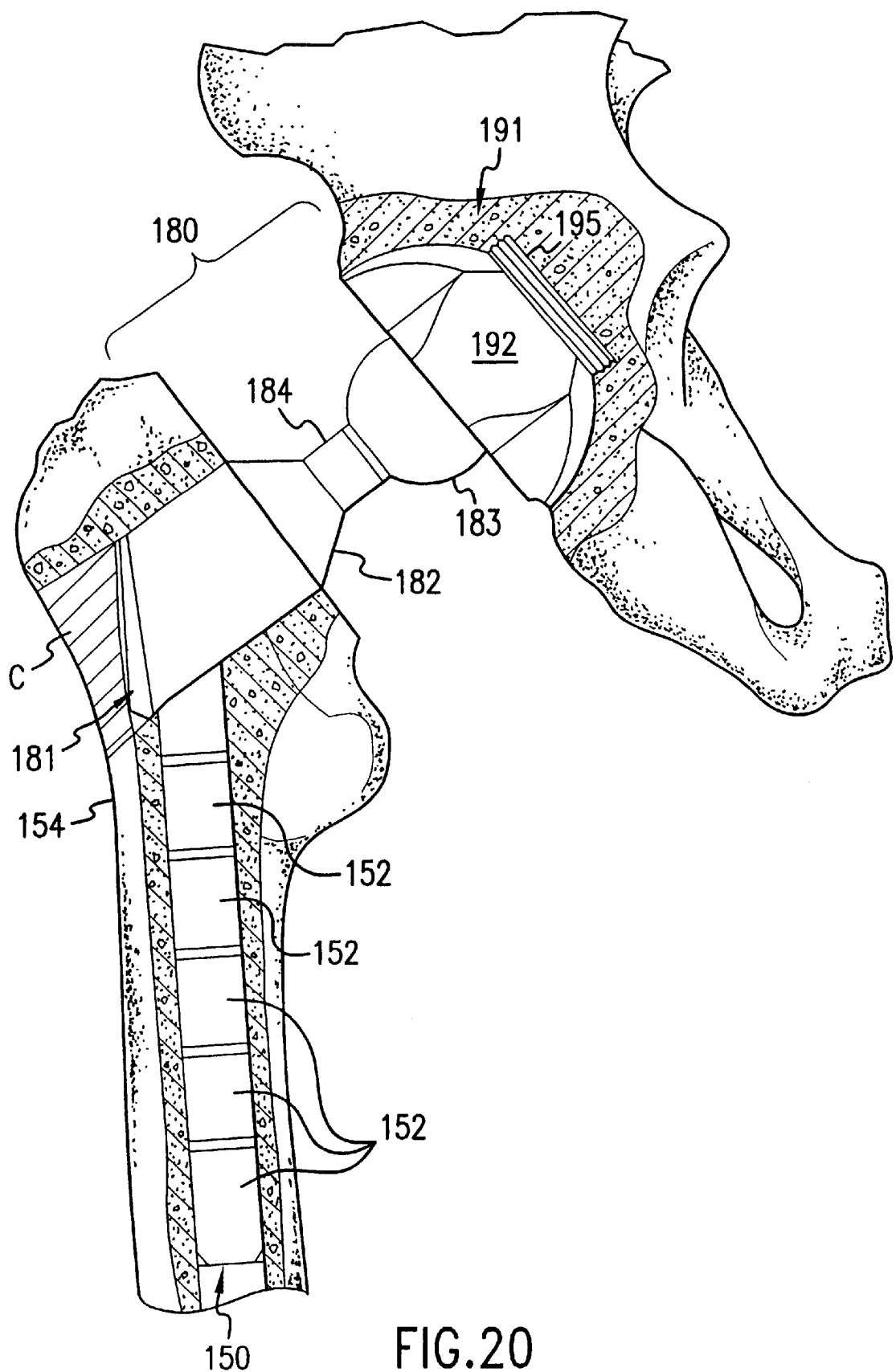
FIG. 20 is a schematic cross-sectional view illustrating on embodiment of a total hip prosthesis as implanted according to the present invention.

In a further exemplary embodiment, the method of the present invention is utilized to perform a non-anatomical total hip arthroplasty in which the femoral head is resected, the acetabulum prepared and the prosthesis implanted via the transosseous core approach. FIG. 20 illustrates schematically femoral and acetabular implants according to the invention, which have been placed via the transosseous core approach of the invention. In this embodiment, a lateral incision is made centered over the greater trochanter. Once soft tissue has been dissected down to the bone as previously described in connection with the shoulder replacement embodiment, appropriately sized core cutting device 30 is inserted through drill guide 22 and a bone core is removed. Because the entire joint is replaced in this procedure, the initial core hole may impinge upon the articular surface. The size of the core through the femur is generally larger than the shoulder core and averages 30 mm in diameter, and typically ranges from 22 mm to 35 mm. After the first core is removed and set aside for later reimplantation, the femoral head is resected and removed though the core hole as described in greater below. Preferably the femoral head is resected relatively perpendicularly to the longitudinal axis of the femoral neck at its neck level (approximately 15 mm above the lesser trochanter). Finally, the acetabulum is reamed to a depth and a diameter as appropriate for acetabular prosthesis to be implanted.

Figure 21:
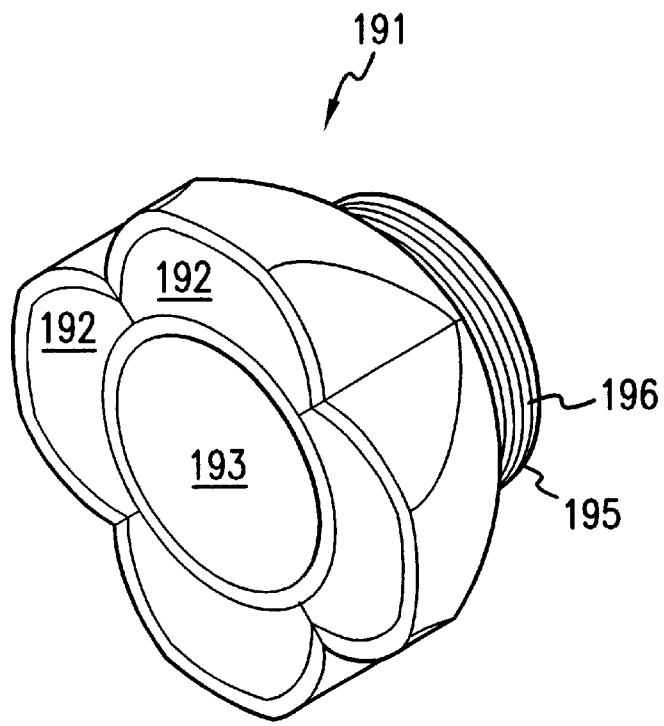
FIG. 21 is perspective view of an acetabular implant according to an embodiment of the present invention.
Figure 22:
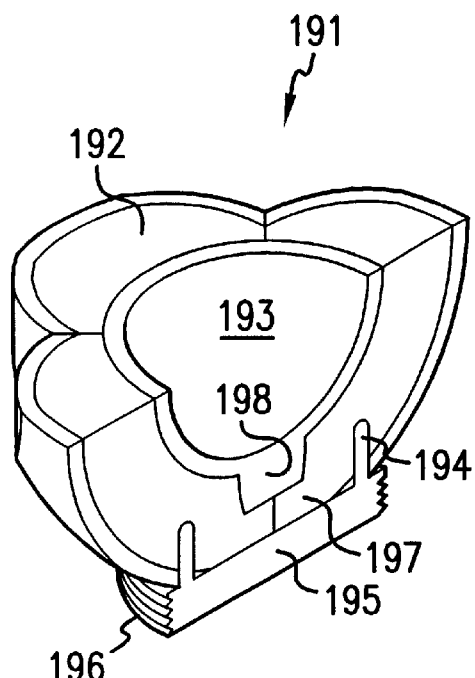
FIG. 22 is a cross-sectional perspective view of the acetabular implant shown in FIG. 21.

Once the bone has been properly prepared, a total hip replacement prosthesis may be implanted. As illustrated in FIG. 20, total hip joint prosthesis assembly 180 according to one embodiment of the present invention includes femoral assembly 181 and acetabular assembly 191. Preferably, base 195 of acetabular assembly 191 (shown also in FIGS. 21 and 22) is inserted through drill guide 22. Threads 196 or other protrusions may be provided to facilitate securing base 195 to the bone. Additionally, provision may be made for screws, other mechanical fixation elements, magnets or adhesives as previously described. Concave acetabular implant modules 192 are inserted and, as best seen in FIG. 22, secured on lip 194 of base 195 side by side. Hemispherical cup 193 is positioned in front of implant modules 194 and cylindrical protrusion 198 is coupled to circular groove 197 of implant modules 192 by interference or pressure fit, thereby assembling acetabular assembly 191 in situ. Other methods of interlocking modules of the assembly can also be used. After implanting acetabular assembly 191, components of femoral assembly 181 are inserted in the order of head 183, neck 184, and core implant module 182. For ease of implantation, neck 184 and core implant module 182 may be made as a unitary article, and head 183 may be attached thereto prior to insertion. The components may be secured together by interference fits as is known in the art and additional mechanical elements such as screws, magnets etc. may be provided for greater security. A stem is inserted which, in this embodiment, is assembled from stem components 152 that are inserted one by one and assembled in situ to form modular stem assembly 150 as previously described. If desired, the implant may use magnets as described in the copending '356 application or may be cemented in place. A portion of bone core C, removed from the femur at the beginning of the procedure may be replaced to close the bone core hole.

Figure 23:
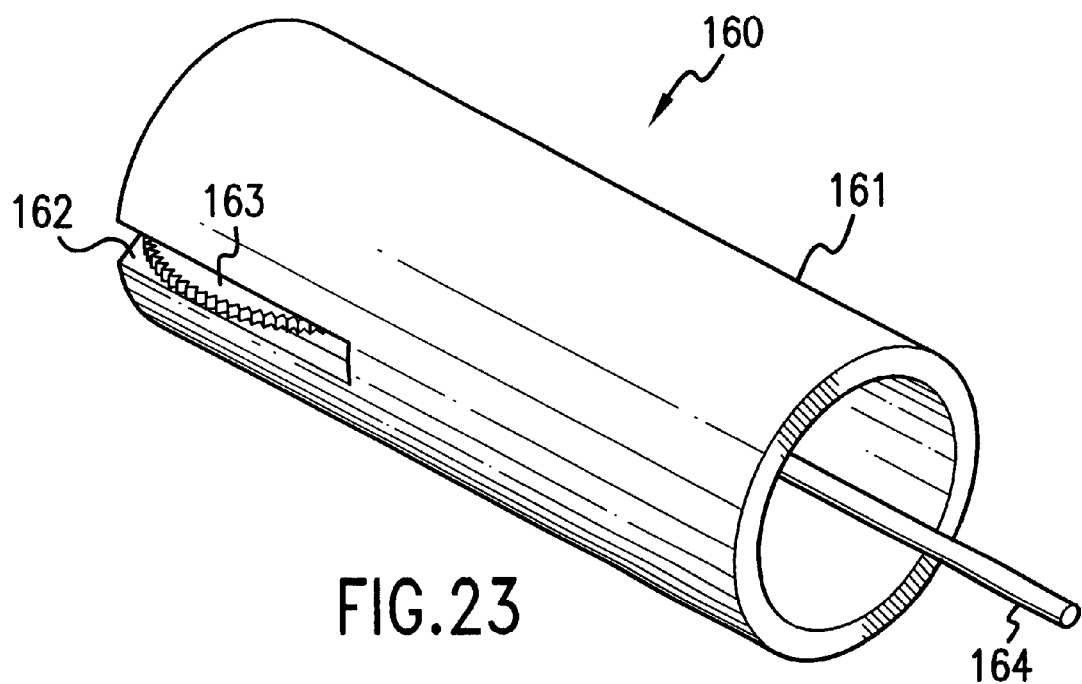
FIG. 23 is a perspective view of an axial retractable cutting device according to an embodiment of the present invention.
Figure 24:
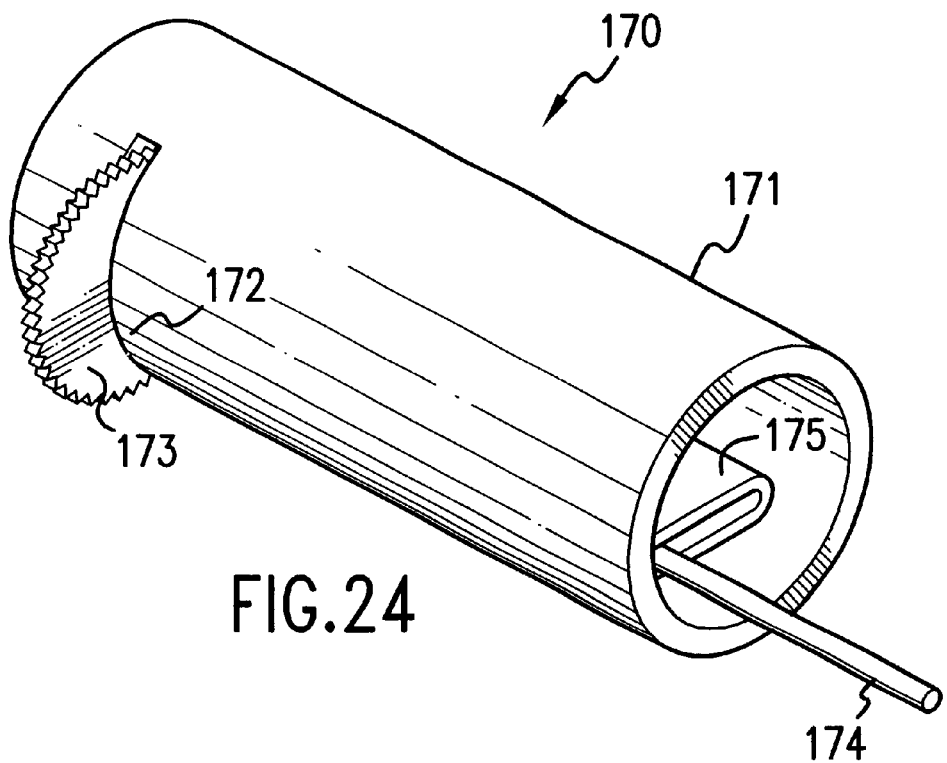
FIG. 24 is a perspective view of an transaxial retractable cutting device according to another embodiment of the present invention.

In order to resect the femoral head as described above, retractable axial cutting device 160 (FIG. 23) and retractable transaxial cutting device 170 (FIG. 24) may be employed according to the present invention. Retractable axial cutting device 160 includes cylindrical body 161 having horizontal slit 162 at its distal end. Circular cutting element 163 is coupled to shaft 164, which is in turn movably retained inside guide 165. Shaft 164 is arranged to move laterally along an internal guide (not shown), thereby moving cutting element 163 between a retracted position (where entire cutting element 163 is retained inside slit 162) and an operating position (where a desirable portion of cutting element 163 protrudes out of slit 162). Although not shown in the figure, a power transmission converts oscillatory or rotational motion of shaft 164 about a longitudinal axis of axial cutting device 160 into another oscillatory or rotational motion of cutting element 163 about an axis perpendicular to the longitudinal axis. Alternatively, a power conveying belt may be used to oscillate or rotate the cutting element. Transaxial cutting device 170 includes cylindrical body 171 forming horizontal slit 172 at its distal end. Circular cutting element 173 is vertically disposed and coupled to shaft 174 movably retained inside guide 175 so as to move cutting element 173 between a retracted position (where entire cutting element 173 is retained inside slit 172) and an operating position (where a desirable portion of cutting element 173 protrudes out of slit 172).

To resect the femoral head, retractable transaxial cutting device 170 is inserted through drill guide 22 and the previously cut bone core hole with cutting element 173 in the retracted position. After positioning transaxial cutting device 170 in the femoral head portion within the core hole, cutting element 173 is engaged and moved to its operating position to separate the femoral head portion from the femur by cutting the hollow femoral neck from the inner surface of the femoral neck to the outer surface thereof by rotating cutting element 173 of transaxial cutting device 170 to make serial cuts. After transacting the femoral head, cutting element 173 is moved to its retracted position and transaxial cutting device 170 is pulled back from the first core hole, leaving the cut and detached femoral head in the joint (which is typically too big to be removed through the first core hole). Retractable axial cutting device 160 is then inserted through drill guide 22 and the first core hole with cutting element 163 in the retracted position. After positioning vertical cutting device 160 inside the transacted femoral head, cutting element 163 is engaged and moved to its operating position to cut the femoral head into multiple smaller portions, e.g., by cutting the femoral head along the longitudinal axis into multiple sections with areas small enough to be removed through the core hole. Axial cutting device 160 is then removed and femoral head portions are taken out by graspers, forceps or clamps. Alternatively, it may be preferable to first use the axial cutting device to make several longitudinal cuts, followed by the transaxial cutting device.

The method and apparatus according to the present invention can generally be applied to any articular joint having at least two major bones. Further examples include, but are not limited to the elbow, wrist, phalanx, knee, and ankle. Moreover, the transosseous core approach according to the invention may be applied in joints involving three or more bones wherein multiple first core or auxiliary holes are provided in one or more more-accessible bones in order to treat single or multiple less accessible bones. For example, the elbow includes two separate articulations, the first between the humerus and radius, and the second between the humerus and ulna. Each of these articulations have surfaces that are subject to individual treatment, potentially requiring multiple core holes to enter the joint at different angles with respect to the long axis of an extended elbow joint. Another example is the knee joint, which also include two separate articulations, the patello-femoral joint and the tibio-femoral joint. The patello-femoral joint consists of one compartment and tibio-femoral joint consists of two compartments. Each of the compartments has articular surfaces that are subject to treatment. Based on the teachings provided herein, a person of ordinary skill in the art may devise an appropriate treatment for any appropriate joint utilizing the advantages of the transosseous core approach and associated instrumentation according to the invention.

In general, the orthopedic surgeon can use the present invention to treat virtually any joint disorder including the results of trauma, instability, early arthritis, end-stage arthritis, tumors, and/or other anatomical abnormalities. The present invention can also be used in trauma management for the treatment of fractures, cartilage damage, and/or other structural damage. In particular, the present invention allows the surgeon to gain access to various joints to repair, replace, treat, manipulate, and/or reinforce the joint structures that have been injured, without the necessity of dislocating the joint and frequently without involving soft tissue structures such as the articular capsule and ligaments. The present invention also permits the surgeon to treat instability, early arthritis, and end-stage arthritis affecting joints by inserting implants that act as additional restraints or as new surfaces for the bones of the joint.

It is to be understood that, while various embodiments of the invention have been described in conjunction with the detailed description thereof, the foregoing is intended only to illustrate and not to limit the scope of the present invention, which is defined by the scope of the appended claims. Other equivalent embodiments, aspects, advantages, and modifications are within the scope of the following claims.

What is claimed is:

1. A method for treating a joint, wherein the joint includes at least one first bone, at least one second adjacent bone and surrounding anatomical structures, and wherein the first bone has an articular surface and a first region, the second bone has an articular surface and a first region, and the second bone articular surface functionally opposes the first bone articular surface, the method comprising:

positioning the first bone with respect to the second bone;

removing a bone core from the first bone along a first axis to provide a bone core hole beginning in the first bone first region and approaching the first bone articular surface without penetrating said articular surface;

performing an intervention through said bone core hole; and reimplanting at least portion of said first bone core within said bone core hole.

2. The method of claim 1, wherein said intervention comprises implanting at least one component of a prosthetic device within said first bone core hole.

3. The method of claim 2, wherein said prosthetic device comprises at least two components and said components are assembled within the bone core hole.

4. The method of claim 2, wherein said prosthetic device includes at least one of:

a magnetic array;

an implant capable of providing mechanical support to the bone; and an agent delivery system capable of delivering at least one agent for treating at least one of the first bone, the second bone, and the surrounding anatomical structures of the joint.

5. The method of claim 4, wherein the agent is a pharmaceutical agent capable of inducing pharmacological intervention in at least one of the bones and the joint.

6. The method of claim 5, wherein the pharmacological agent is at least one of steroids, antibiotics and chemotherapeutics.

7. The method of claim 4, wherein the agent is a fluid agent capable of providing rheological intervention to the first bone, the second bone, and the surrounding anatomical structures of the joint.

8. The method of claim 1, wherein said removing bone comprises:

positioning a guide assembly in the first region of the first bone;

inserting a cutting element through the guide assembly; and engaging the cutting element to cut the first core hole in the first bone.

9. The method of claim 1, further comprising cutting away bone material in at least one of said bones in a direction away from the first axis and removing said cut away bone material through said bone core hole in said first bone to provide a cavity of larger dimension than the core hole.

10. The method of claim 9, wherein said cutting comprises removing an end portion of at least one of said bones.

11. The method of claim 10, further comprising replacing said bone end portion with a first implant inserted through said bone core hole.

12. The method of claim 1, wherein said first region is a non-articular bone surface.

13. The method of claim 1, wherein said first region is an articular bone surface.

14. The method of claim 1 further comprising:

cutting the first bone starting from a second region of the first bone; and ceasing cutting after reaching a depth without cutting the first articular surface, thereby providing the first bone with an elongated first auxiliary hole configured to receive an implant.

15. The method of claim 14, wherein the second region is an articular bone surface or a non-articular bone surface.

16. The method of claim 15, further comprising:

inserting at least one first auxiliary implant through the first auxiliary hole; and securing the first auxiliary implant to the first auxiliary hole.

17. The method of claim 1, wherein said intervention comprises treating intra-joint soft tissue structures through said bone core hole.

18. A method for treating a joint, wherein the joint includes at least one first bone, at least one second adjacent bone and surrounding anatomical structures, and wherein the first bone has an articular surface and a first region, the second bone has an articular surface and a first region, and the second bone articular surface functionally opposes the first bone articular surface, the method comprising:

positioning the first bone with respect to the second bone;

removing a bone core from the first bone along a first axis to provide a bone core hole;

removing the bone core through the first articular surface;

preserving a cut-out core portion of the first articular surface;

performing an intervention through said bone core hole;

subsequent to said intervention inserting at least a part of the cut-out core portion through the first core hole; and reimplanting the cut-out core portion at the first articular surface.

19. The method of claim 18, further comprising an additional step of removing the bone core through said first bone articular surface and into said second bone, said core hole terminating within said second bone.

20. The method of claim 19, further comprising:

preserving a cut-out core portion of the second articular surface;

inserting at least a part of the cut-out core portion through the first core hole after said intervention; and reimplanting the cut-out core portion at the second articular surface.

21. The method of claim 19, wherein said intervention comprises placing at least one component of a prosthetic implant in the second bone though said first bone core hole.

22. The method of claim 21, wherein said positioning comprises:

inserting a guide wire into the first bone, entering from the first region of the first bone and approaching the first articular surface of the first bone; and movably positioning at least one guide assembly and cutting element over the guide wire.

23. The method of claim 19, wherein said intervention comprises treating intra-joint soft tissue structures through said bone core hole.

24. The method of claim 18, further comprising cutting away bone material in at least one of said bones in a direction away from the first axis and removing said cut away bone material through said bone core hole in said first bone to provide a cavity of larger dimension the core hole.

25. The method of claim 24, wherein said cutting comprises removing an end of at least one of said bones.

26. The method of claim 25, further comprising replacing said bone end portion with a first prosthetic implant inserted through said bone core hole.

27. The method of claim 26, wherein said step of removing a bone core further comprises removing the bone core through said first bone articular surface and continuing cutting into said second bone, and said method further comprises placing a second prosthetic implant in the second bone though said first bone core hole, said first and second prosthetic implants cooperating to facilitate joint function.

28. The method of claim 18, wherein said intervention comprises implanting a prosthetic with at least one articular surface.

29. A method for treating a joint, said joint including at least one first bone, at least one second adjacent bone and surrounding anatomical structures, wherein the first bone has an articular surface and a first region, the second bone has an articular surface and a first region, and the second bone articular surface functionally opposes the first bone articular surface, the method comprising:

positioning the first bone with respect to the second bone;

cutting a hole in the first bone along a first axis beginning in the first bone first region and passing through the first bone articular surface;

continuing cutting said hole through the second bone articular surface and into said second bone;

terminating cutting of said hole within the second bone; and implanting at least one component of a prosthetic device within the second bone hole by passing said at least one component through said first bone hole.

30. The method of claim 29, further comprising cutting away bone material in at least one of said bones in a direction away from the first axis and removing said cut away bone material through said hole in said first bone to provide a cavity of larger dimension than the hole.

31. The method of claim 29, wherein:

said prosthetic device comprises multiple components; and said implanting comprises assembling said multiple components together to form the prosthetic device within the bone hole.

32. The method of claim 29, wherein said cutting comprises coring the bone to provide a bone core suitable for at least partial replacement.

33. The method of claim 29, further comprising:

changing the position of the first bone with respect to the second bone;

cutting out a second portion of the second articular surface through the first bone hole;

cutting a second hole in the second bone and into an interior thereof through the first bone hole; and ceasing cutting after reaching a predetermined depth, thereby providing the second bone with a second hole.

34. The method of claim 29, wherein the implanting of said at least one component of a prosthetic device comprises a prosthesis that replaces at least part of one of said articular surfaces.

35. A method for treating a joint, said joint including at least one first bone, at least one second adjacent bone and surrounding anatomical structures, wherein the first bone has an articular surface and a first region, the second bone has an articular surface and a first region, the method comprising:

positioning the first bone with respect to the second bone;

cutting a hole having a first diameter in the first bone along a first axis beginning in the first bone first region and passing through the first bone articular surface;

continuing cutting said hole through the second bone articular surface and into said second bone;

enlarging said hole to a second diameter greater than the first diameter at a location spaced away from the first bone first region; and implanting at least one component of a prosthetic device within the enlarged hole by passing said at least one component through said hole with the first diameter.

36. The method according to claim 35, wherein said prosthetic device comprises plural implant modules, said modules being sized to be passed through said first diameter bone hole, said method further comprising:

inserting each module individually through said first diameter bone hole; and assembling the prosthetic device implant modules within the second diameter bone hole.

37. The method according to claim 36, wherein:

said enlarging comprises resecting a terminal end portion of at least one bone, including the associated articular surface and removing resected materials through the first diameter bone hole; and said prosthetic device comprises a total joint prosthesis.

38. The method according to claim 36, wherein at least one of said bones includes an intramedullary canal and said method further comprises:

inserting a tool through said first diameter bone hole and into the intramedullary canal;

preparing the intramedullary canal with said tool;

inserting segments of an intramedullary rod into said canal through the first diameter bone hole; and assembling said intramedullary rod in the intramedullary canal.

39. The method according to claim 36, wherein the joint is a shoulder and the prosthetic device comprises a humeral component and a glenoid component.

40. The method according to claim 39, wherein each said component comprises plural implant modules, said method further comprising inserting, assembling and implanting said glenoid component modules followed by inserting, assembling and implanting said humeral component modules.

41. The method according to claim 36, wherein the joint is a hip and the prosthetic device comprises a femoral component and an acetabular component.

42. The method according to claim 41, wherein each said component comprises plural implant modules, said method further comprising inserting, assembling and implanting said acetabular component followed by inserting, assembling and implanting said formal component.

* * * * *